US010786349B2

(12) United States Patent
Remenschneider et al.

(10) Patent No.: US 10,786,349 B2
(45) Date of Patent: Sep. 29, 2020

(54) ARTIFICIAL TYMPANIC MEMBRANE DEVICES AND USES

(71) Applicants: Massachusetts Eye and Ear Infirmary, Boston, MA (US); President and Fellows of Harvard College, Cambridge, MA (US)

(72) Inventors: Aaron K. Remenschneider, Boston, MA (US); Elliot Kozin, Boston, MA (US); Nicole Black, Shelby Township, MI (US); Michael J. McKenna, Southborough, MA (US); Daniel J. Lee, Brookline, MA (US); Jennifer Lewis, Cambridge, MA (US); John Rosowski, Arlington, MA (US); David Kolesky, Cambridge, MA (US); Mark A. Skylar-Scott, Brookline, MA (US); Alexander D. Valentine, Windham, NH (US)

(73) Assignees: Massachusetts Eye and Ear Infirmary, Boston, MA (US); President and Fellows of Harvard College, Cambridge, MA (US)

( * ) Notice: Subject to any disclaimer, the term of this patent is extended or adjusted under 35 U.S.C. 154(b) by 211 days.

(21) Appl. No.: 15/559,582

(22) PCT Filed: Mar. 21, 2016

(86) PCT No.: PCT/US2016/023482
§ 371 (c)(1),
(2) Date: Sep. 19, 2017

(87) PCT Pub. No.: WO2016/154148
PCT Pub. Date: Sep. 29, 2016

(65) Prior Publication Data
US 2018/0042718 A1 Feb. 15, 2018

Related U.S. Application Data

(60) Provisional application No. 62/247,268, filed on Oct. 28, 2015, provisional application No. 62/245,827, (Continued)

(51) Int. Cl.
*A61F 2/18* (2006.01)
*A61L 27/26* (2006.01)
(Continued)

(52) U.S. Cl.
CPC ............... *A61F 2/18* (2013.01); *A61L 27/26* (2013.01); *A61L 27/3839* (2013.01);
(Continued)

(58) Field of Classification Search
CPC ...... A61L 27/26; A61L 27/3839; A61L 27/54; A61F 2230/0067; A61F 2230/0006; A61F 2250/0067; A61F 2/18
(Continued)

(56) References Cited

U.S. PATENT DOCUMENTS

| 4,014,971 A | 3/1977 | Rodney |
| 5,007,934 A | 4/1991 | Stone |

(Continued)

FOREIGN PATENT DOCUMENTS

| CN | 2162943 | 4/1994 |
| JP | S50-031693 | 3/1975 |

(Continued)

OTHER PUBLICATIONS

Barry III et al., "Direct-Write Assembly of 3D Hydrogel Scaffolds for Guided Cell Growth. Advanced Materials," 2009, 21:2407-2410.

(Continued)

*Primary Examiner* — Suba Ganesan
*Assistant Examiner* — Aren Patel
(74) *Attorney, Agent, or Firm* — Fish & Richardson P.C.

(57) ABSTRACT

This disclosure features artificial tympanic membrane graft devices and two-component bilayer graft devices that include a scaffold having a plurality of ribs made of a first material and a plurality of spaces between the ribs filled or made with the first material, a different, second material, a (Continued)

combination of the first and a second materials, or a combination of a second material and one or more other different materials. The bilayer graft devices have two components or layers. One component, e.g., the underlay graft device, can include a projection, and the second component, e.g., the overlay graft device, can include an opening that corresponds to the projection (or vice versa) so that the opening and the projection can secure the two layers together in a "lock and key" manner. This disclosure also features methods of making, using, and implanting the three-dimensional artificial tympanic membrane and bilayer graft devices.

23 Claims, 26 Drawing Sheets

Related U.S. Application Data filed on Oct. 23, 2015, provisional application No. 62/136,097, filed on Mar. 20, 2015.

(51) Int. Cl.
*A61L 27/38* (2006.01)
*A61L 27/54* (2006.01)

(52) U.S. Cl.
CPC ......... *A61L 27/54* (2013.01); *A61F 2002/183* (2013.01); *A61F 2230/0006* (2013.01); *A61F 2230/0067* (2013.01); *A61F 2250/0067* (2013.01); *A61L 2430/14* (2013.01)

(58) Field of Classification Search
USPC .......................................................... 623/10
See application file for complete search history.

(56) References Cited

U.S. PATENT DOCUMENTS

| | | | |
|---|---|---|---|
| 5,501,700 A | 3/1996 | Hirata | |
| 6,309,419 B1 | 10/2001 | Eugene et al. | |
| 8,197,433 B2 | 6/2012 | Cohen | |
| 8,480,610 B1 | 7/2013 | Hill | |
| 2003/0018291 A1 | 1/2003 | Hill et al. | |
| 2005/0075733 A1 | 4/2005 | D'Eredita | |
| 2006/0142736 A1 | 6/2006 | Hissink et al. | |
| 2008/0234817 A1* | 9/2008 | Huettenbrink | A61F 2/18 623/10 |
| 2008/0268016 A1* | 10/2008 | Fang | A61K 35/22 424/423 |
| 2012/0191030 A1 | 7/2012 | Avior | |
| 2013/0345722 A1 | 12/2013 | Margulis | |
| 2014/0012282 A1 | 1/2014 | Michael | |
| 2014/0094910 A1* | 4/2014 | Steinhardt | A61F 2/18 623/10 |
| 2014/0194891 A1 | 7/2014 | Shahoian | |
| 2014/0257518 A1* | 9/2014 | McAlpine | A61L 27/14 623/24 |
| 2014/0303728 A1* | 10/2014 | Steinhardt | A61F 2/18 623/10 |

FOREIGN PATENT DOCUMENTS

| | | |
|---|---|---|
| JP | 2011-110204 A | 6/2011 |
| WO | WO 2011/142425 | 11/2011 |

OTHER PUBLICATIONS

Boedts et al., "A scanning electron-microscopic study of different tympanic grafts," Am J Otol, 1990, 11(4):274-277.
Calobrace, "The design and engineering of the MemoryShape breast implant." Plast Reconstr Surg, 2014, 134(3 Suppl): 10S-15S.
Cheng et al., "Motion of the surface of the human tympanic membrane measured with stroboscopic holography," Hear Res, 2010, 263(1-2):66-77.
Cheng et al., "Wave motion on the surface of the human tympanic membrane: holographic measurement and modeling analysis," J Acoust Soc Am, 2013, 133(2):918-937.
Cranford et al., "Nonlinear material behaviour of spider silk yields robust webs," Nature, 2012, 482(7383):72-76.
Decraemer et al., "Shape and derived geometrical parameters of the adult, human tympanic membrane measured with a phase-shift moire interferometer," Hear Res, 1991, 51(1):107-121.
Dvorak, et al., "Repair of chronic tympanic membrane perforations with long-term epidermal growth factor," Laryngoscope, 1995, 105(12 Pt 1): 1300-1304.
Ensari, "Effects of polylactic acid film on middle ear mucosa and cochlear function in Guinea pigs," Eur Arch Otorhinolaryngol, 2015, 272(5): 1091-1097.
Fernandes, "Composite chondroperichondrial clip tympanoplasty: The 1-6, 7/1-7/6 triple "C" technique," Otolaryngology Head Neck Surgery, 2003, 128: 267-272.
Geckil et al., "Engineering hydrogels as extracellular matrix mimics," Nanomedicine (Lond), 2010, 5(3):469-484.
Gersdorff, et al., "Overlay versus underlay tympanoplasty. Comparative study of 122 cases," Rev Laryngol Otol Rhinol (Bord), 2003, 124(1): 15-22.
Ghanem, et al., "Butterfly cartilage graft inlay tympanoplasty for large perforations," Laryngoscope, 2006, 116(10): 1813-1816.
Gratson et al., "Microperiodic structures: direct writing of three-dimensional webs," Nature, 2004, 428(6981):386.
Hanson Shepherd et al., "3D Microperiodic Hydrogel Scaffolds for Robust Neuronal Cultures," Adv Funct Mater, 2011, 21:47-54.
Hardman et al., "Tympanoplasty for Chronic Tympanic Membrane Perforation in Children: Systematic Review and Meta-analysis," Otol Neurotol. 2015, 36(5):796-804.
Hiraide et al., "The fiber arrangement of the pathological human tympanic membrane," Arch Otorhinolaryngol, 1980, 226(1-2):93-99.
Hod et al., "Inlay "butterfly" cartilage tympanoplasty," Am J Otolaryngol, 2013, 34(1): 41-43.
Hong et al., "Repair of tympanic membrane perforation using novel adjuvant therapies: a contemporary review of experimental and tissue engineering studies," Int J Pediatr Otorhinolaryngol, 2013, 77(1): 3-12.
House et al., "Incus homografts in chronic ear surgery," Arch Otolaryngol, 1966, 84(2):148-53.
International Search Report and Written Opinion in International Application No. PCT/US16/23482, dated Jun. 20, 2016, 10 pages.
Jang et al., "Regeneration of chronic tympanic membrane perforation using 3D collagen with topical umbilical cord serum," International Journal of Biological Macromolecules, 2013, 62: 232-240.
Kaylie et al., "Revision chronic ear surgery," Otolaryngol Head Neck Surg, 2006, 134(3):443-50.
Khanna and Tonndorf, "Tympanic membrane vibrations in cats studied by time-averaged holography," J Acoust Soc Am, 1972, 51:1904-20.
Kim et al., "Functional and Practical Outcomes of Inlay Butterfly Cartilage Tympanoplasty." Otol Neurotol, 2014, 35: 1458-1462.
Kohn et al., "New perspectives in myringoplasty," Int J Artif Organs, 1984, 7(3):151-62.
Kozin et al., "Design, fabrication, and in vitro testing of novel three-dimensionally printed tympanic membrane grafts," Hear Res, Oct. 2016, 340: 191-203.
Kozin et al., Theoretical and Practical Considerations of 3-Dimensionally Printed Biomimetic Tympanic Membrane Grafts: Preliminary Design, Manufacture, and Acoustic Testing. Middle Ear Mechanics and Research in Otology, 2015, M. Gaihede. Aalborg, Denmark, MEMRO, 3 pages.
Levin et al., "Grafts in myringoplasty utilizing a silk fibroin scaffold as a novel device," Expert Rev Med Devices, 2009, 6(6):653-64.
Lewis, "Direct Ink Writing of 3D Functional Materials," Advanced Functional Materials, 2006, 16:2193-204.
Lim, "Structure and function of the tympanic membrane: a review," Acta oto-rhino-laryngologica Belgica, 1995, 49(2):101-15.

(56) References Cited

OTHER PUBLICATIONS

Lukasiak et al., "Biodegradation of Silicones (Organosiloxanes)," 2005, 52 pages.
Marquet, "Human middle ear transplants," J Laryngol Otol, 1971, 85(6):523-39.
Minoda et al., "External auditory canal stenting utilizing a useful rolled, tapered silastic sheet (RTSS) post middle ear surgery," Auris Nasus Larynx, 2010, 37(6): 680-684.
Mironov et al., "Organ printing: computer-aided jet-based 3D tissue engineering," Trends in Biotechnology, 2003, 21(4):157-61.
Mota et al., "Multiscale fabrication of biomimetic scaffolds for tympanic membrane tissue engineering," Biofabrication, May 2015, 7: 025005.
Murphy and Atala, "3D bioprinting of tissues and organs," Nat Biotechnol, 2014, 32(8):773-85.
Nadol et al., "Cellular immunologic responses to cochlear implantation in the human," Hear Res, 2014, 318: 11-17.
Parekh et al., "Repair of the tympanic membrane with urinary bladder matrix," Laryngoscope, 2009, 119(6): 1206-1213.
Park et al., "Predictors for outcome of paper patch myringoplasty in patients with chronic tympanic membrane perforations," Eur Arch Otorhinolaryngol, 2015, 272(2): 297-301.
Pfaltz and Griesemer, "Pericard: a new biometerial for tympanoplasty: preliminary report," Am J Otolaryngol, 1985, 6(3):266-8.
Qin et al., "Structural optimization of 3D-printed synthetic spider webs for high strength. Nature communications," 2015, 6:7038.
Rosowski et al., "New data on the motion of the normal and reconstructed tympanic membrane," Otol Neurotol. 2011, 32(9):1559-67.
Rosowski et al., "Computer-assisted time-averaged holograms of the motion of the surface of the mammalian tympanic membrane with sound stimuli of 0.4-25 kHz," Hear Res, 2009, 253(1-2):83-96.
Seliktar, "Designing cell-compatible hydrogels for biomedical applications," Science, 2012, 336(6085):1124-8.
Seyyedi and Nadol, Jr., "Intracochlear Inflammatory Response to Cochlear Implant Electrodes in Humans," Otol Neurotol, 2014, 35: 1545-1551.
Shimada and Lim, "The fiber arrangement of the human tympanic membrane. A scanning electron microscopic observation," Ann Otol Rhinol Laryngol, 1971, 80(2):210-7.
Sun et al., "Direct-Write Assembly of 3D Silk/hydroxyapatite Scaffolds for Bone Co-Cultures," Advanced Healthcare Materials, 2012, 1:729-35.
Tamimi et al., "Osseointegration of dental implants in 3D-printed synthetic onlay grafts customized according to bone metabolic activity in recipient site," Biomaterials, 2014, 35(21): 5436-5445.
Tonndorf and Khanna, "The role of the tympanic membrane in middle ear transmission," Ann Otol, 1970, 79:743-53.
Tonndorf and Khanna, "Tympanic-membrane vibrations in human cadaver ears studied by time-averaged holography," J Acoust Soc Am, 1972, 52:1221-33.
Uebersax et al., "Biocompatibility and osteoconduction of macroporous silk fibroin implants in cortical defects in sheep," Eur J Pharm Biopharm, 2013, 85(1):107-18.
Ulku et al., "Comparisons of the mechanics of partial and total ossicular replacement prostheses with cartilage in a cadaveric temporal bone preparation," Acta Otolaryngol, 2014, 134(8):776-84.
Villar-Fernandez et al., "Outlook for tissue engineering of the tympanic membrane," Audiology Research, Jan. 2015, 5: 117.
Weber et al., "Tissue-engineered calcium alginate patches in the repair of chronic chinchilla tympanic membrane perforations," Laryngoscope, 2006, 116(5): 700-704.
Wehrs, "Grafting techniques," Otolaryngol Clin North Am, 1999, 32(3): 443-455.
Wieland et al., "Poly(glycerol sebacate)-engineered plugs to repair chronic tympanic membrane perforations in a chinchilla model," Otolaryngol Head Neck Surg, 2010, 143(1): 127-133.
Wrzeszcz, et al., "Hydrogel coated and dexamethasone releasing cochlear implants: quantification of fibrosis in guinea pigs and evaluation of insertion forces in a human cochlea model," J Biomed Mater Res B Appl Biomater, 2015, 103(1): 169-178.
Zhang and Gan, "A comprehensive model of human ear for analysis of implantable hearing devices," IEEE Trans Biomed Eng, 2011, 58(10):3024-7.
AU Office Action in AU Application No. 2016235333, dated Jan. 15, 2020, 5 pages.
EP Extended Search Report in European Appln. No. 16769523.8, dated Oct. 25, 2018, 8 pages.
EP Extended Search Report in European Appln. No. 17851503.7, dated Sep. 9, 2019, 7 pages.
EP Office Action in Appln. No. 17851503.7, dated Sep. 30, 2019, 8 pages.
JP Office Action in Japanese Appln. No. 2017-549395, dated Jan. 7, 2020, 15 pages (with English translation).
Levin et al., "Preliminary results of the application of a silk fibroin scaffold to otology," Otolaryngology—Head and Neck Surgery, Mar. 2010, 142(3_suppl):S33-5.
PCT International Preliminary Report on Patentability in international Application No. PCT/US2016/023482, dated Jun. 20, 2016, 9 pages.
PCT International Preliminary Report on Patentability in international Application No. PCT/US2017/051501, dated Mar. 19, 2019, 8 pages.
PCT International Search report and Written Opinion in International Application No. PCT/US2016/023482, dated Jun. 20, 2016, 14 pages.
PCT International Search report and Written Opinion in International Application No. PCT/US2017/051501, dated Nov. 29, 2017, 14 pages.
Teh et al., "Tissue Engineering of the Tympanic Membrane," Tissue Engineering Part B: Reviews, Apr. 1, 2013, 19(2): 116-32.

\* cited by examiner

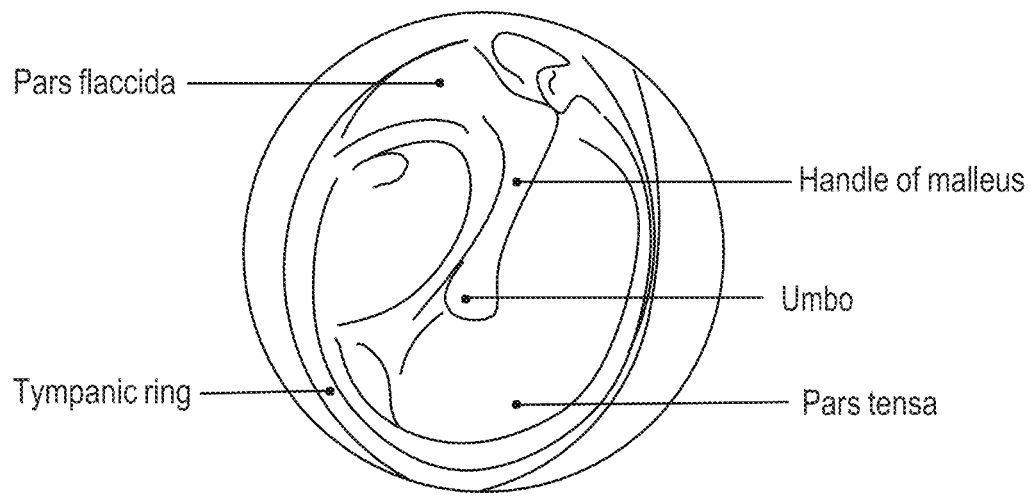
FIG. 1A

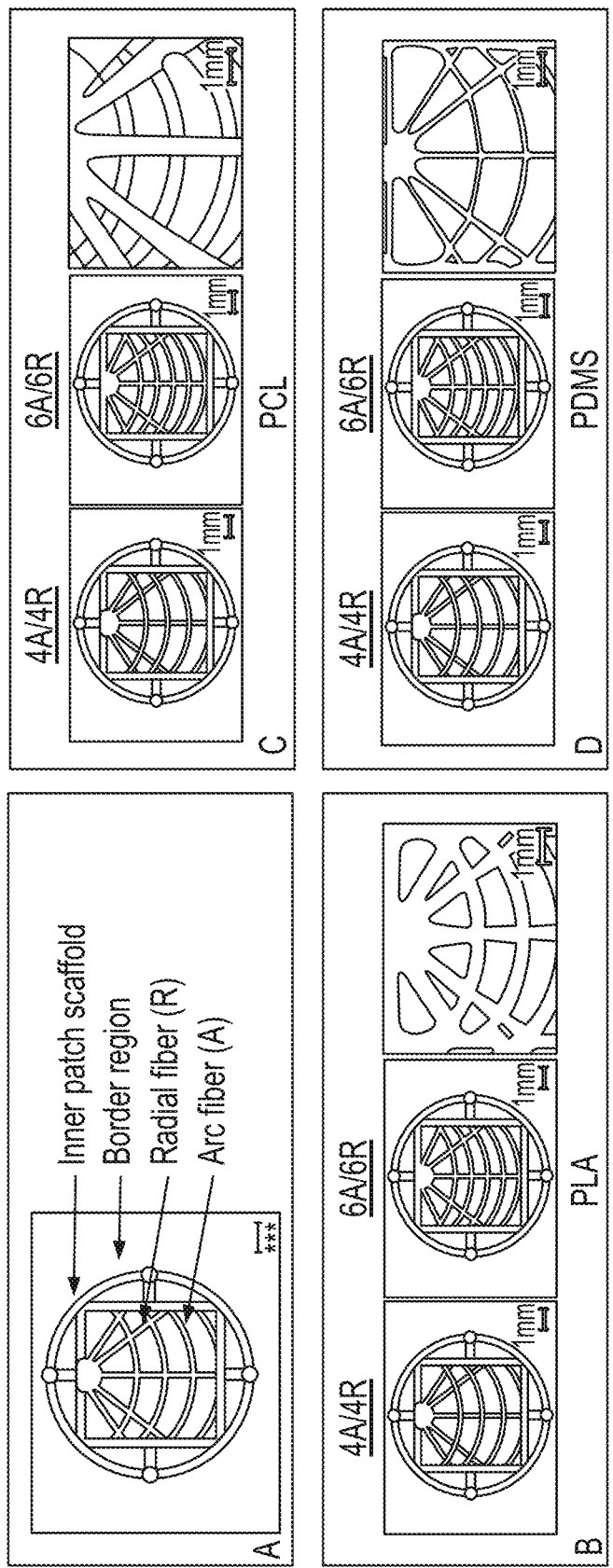

Figure 5. Final Patch Design: Tunable Arc Patches. Features of the tunable arc design include a variable number of equally spaced arcs "A" and radii "R" (A). The rapid tunability of this design allows for flexibility in fiber arrangement and size, depending upon the clinical need and location of perforation. Tunable arc patches were printed in three different materials: PLA (B), PCL (C), and PDMS (D). Due to modest differences in ink rheology, PDMS prints the finest resolution filaments, PLA intermediate, and PCL in coarse and slightly irregular filaments.

FIG. 2E

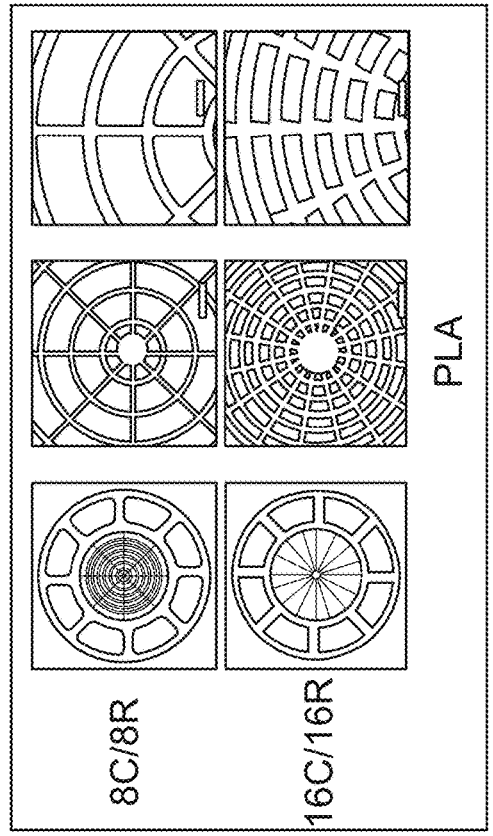
FIG 3B-B
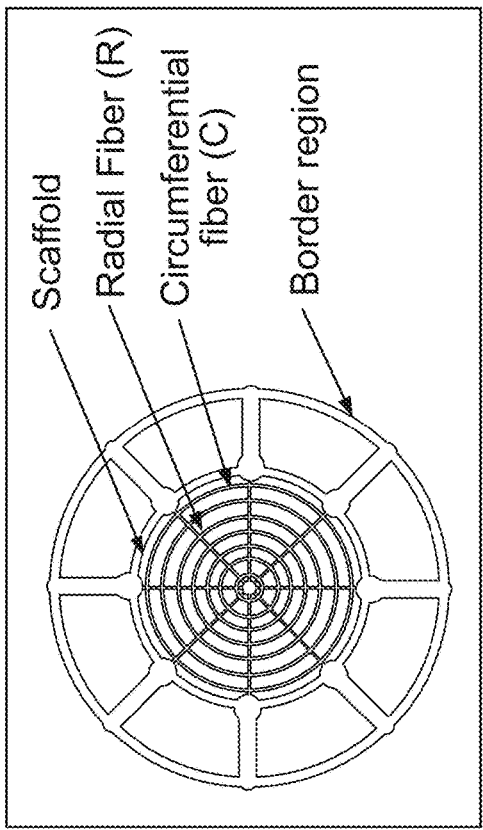
FIG 3B-D
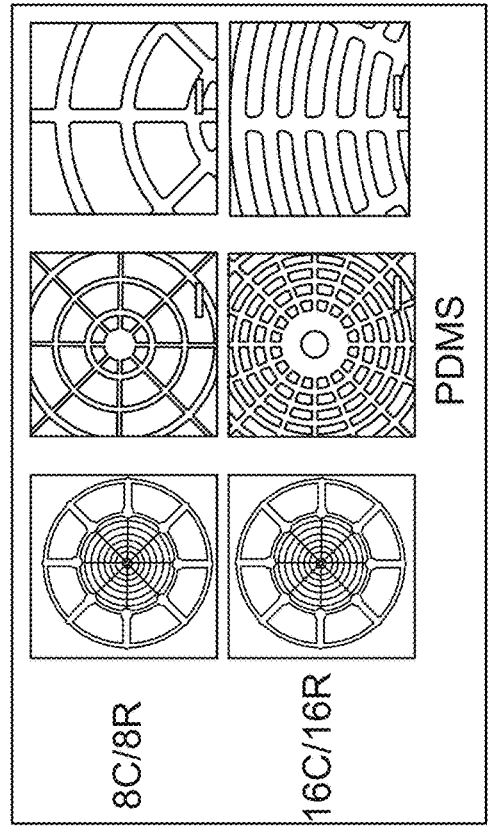
FIG 3B-A
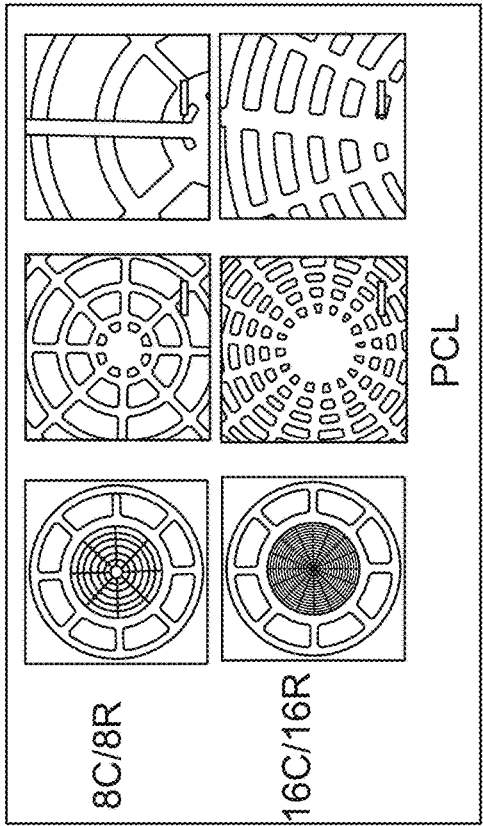
FIG 3B-C

WITH BORDER
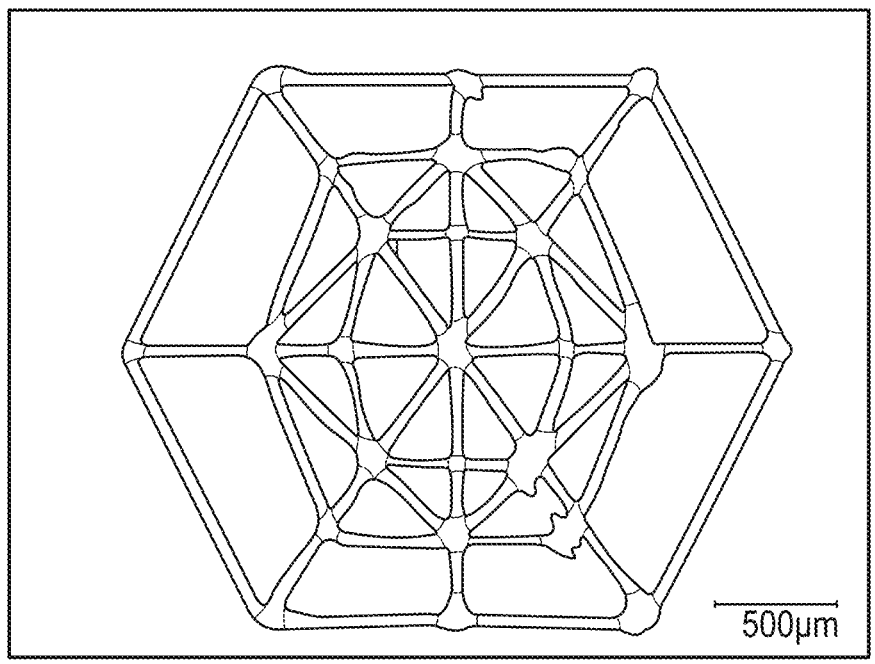
FIG. 3C-A
WITHOUT BORDER
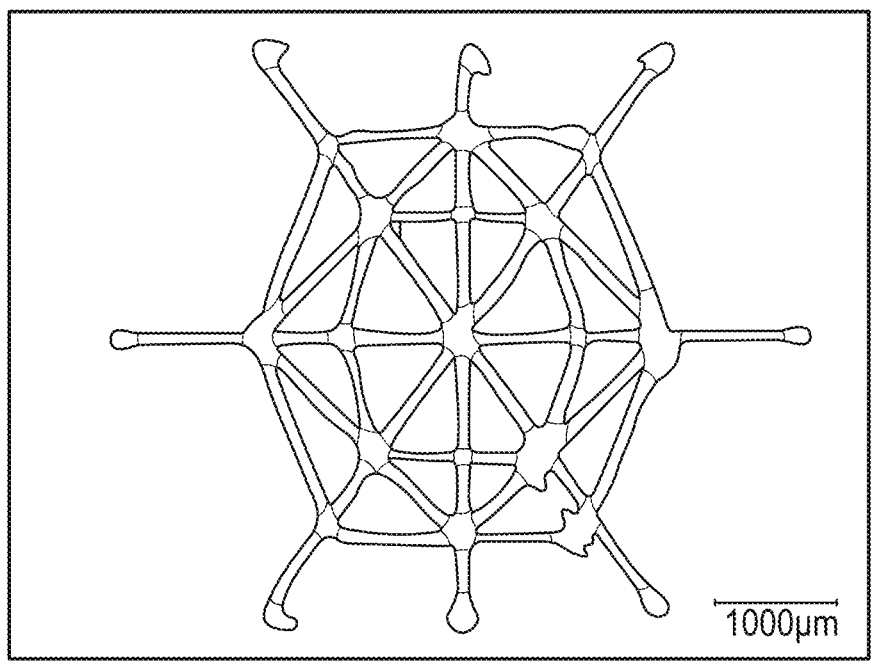
FIG. 3C-B

Underlay

Overlay

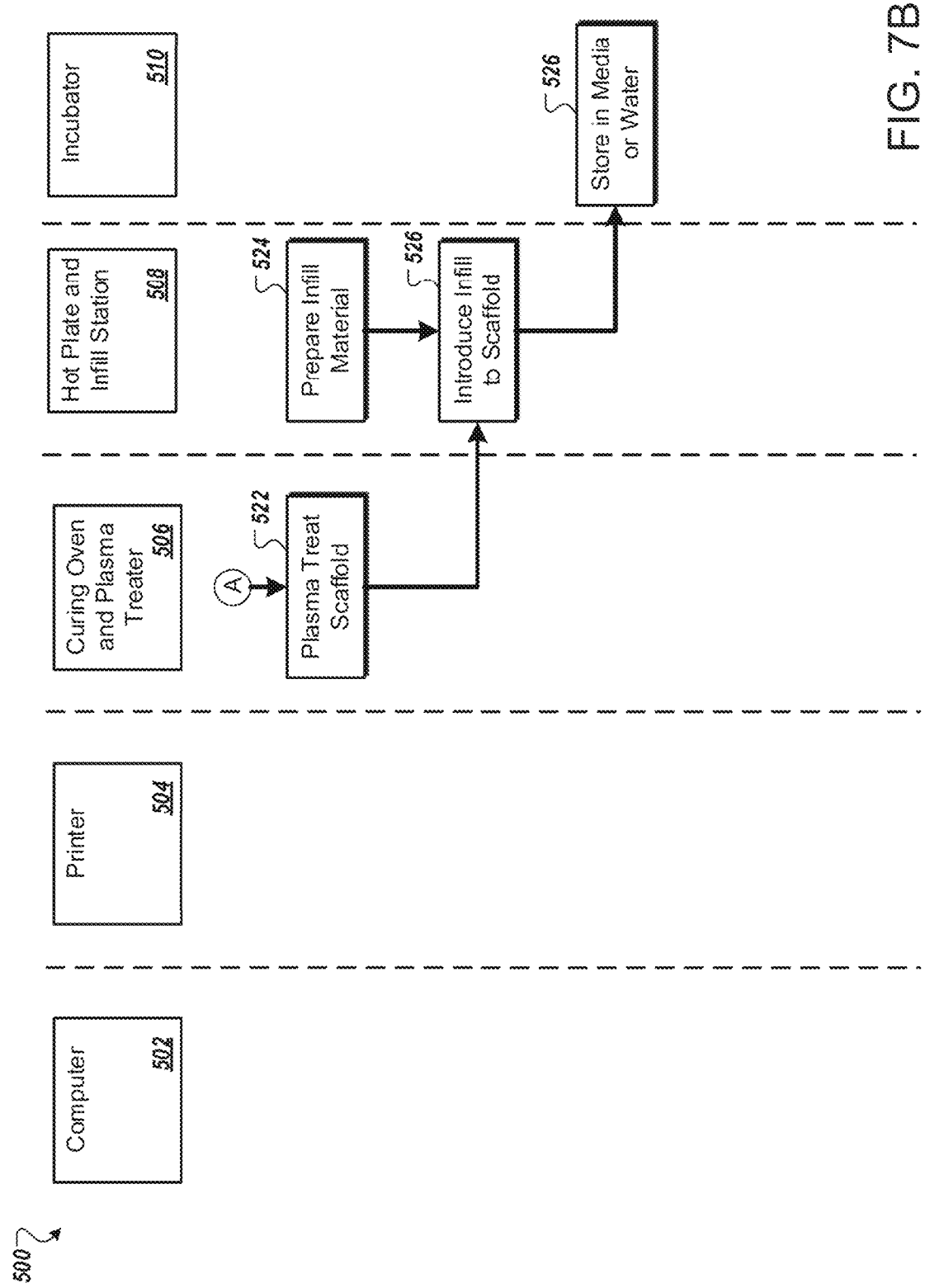

Fiber arrangement template

Tympanic Membrane Perforation

Customized 3D printed patch

Repair

Displacement normalized by sound pressure: 1000 Hz

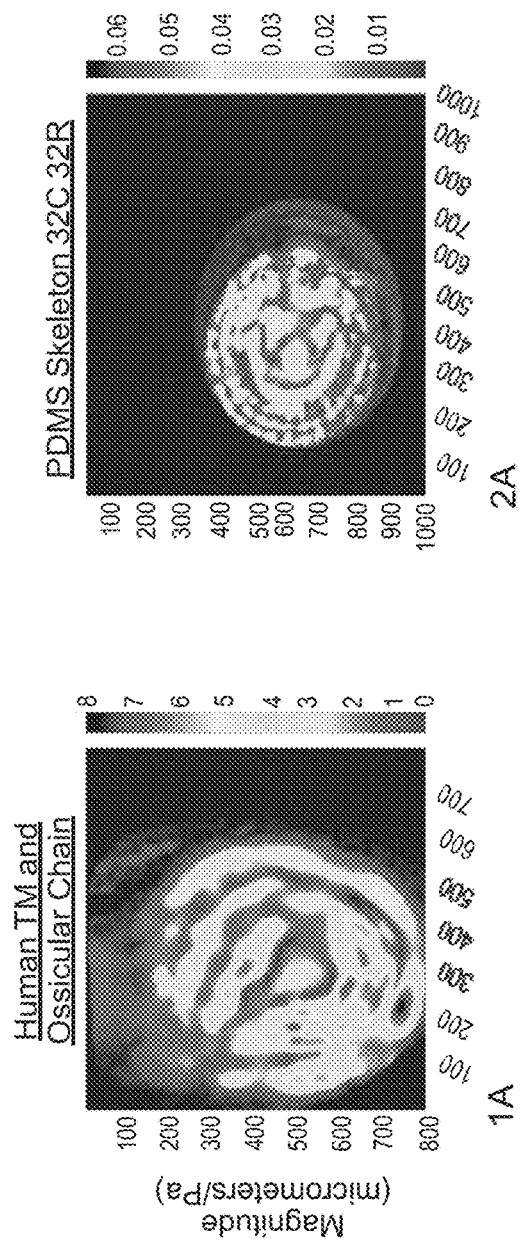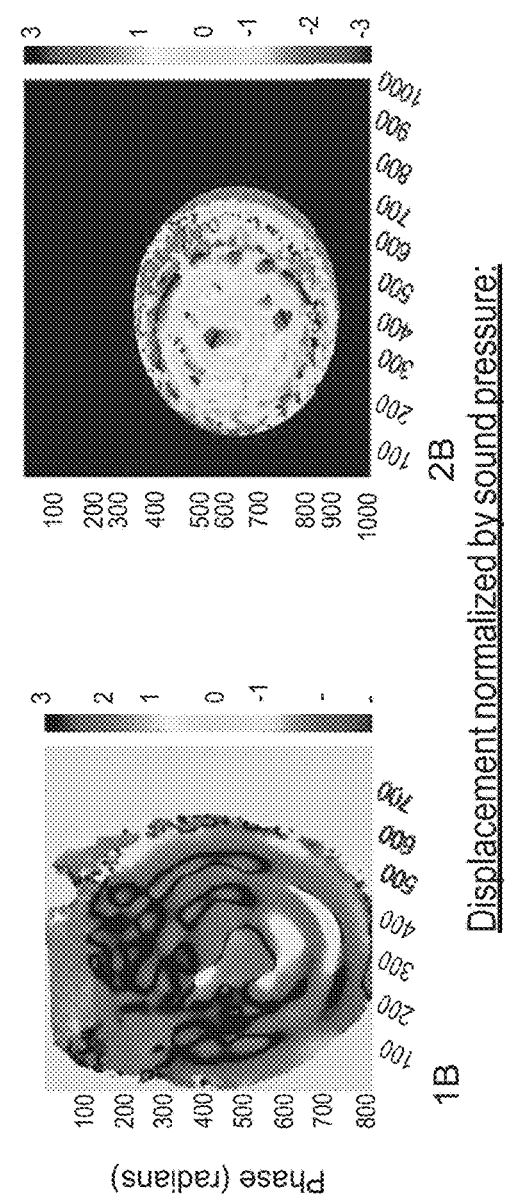
FIG. 12D

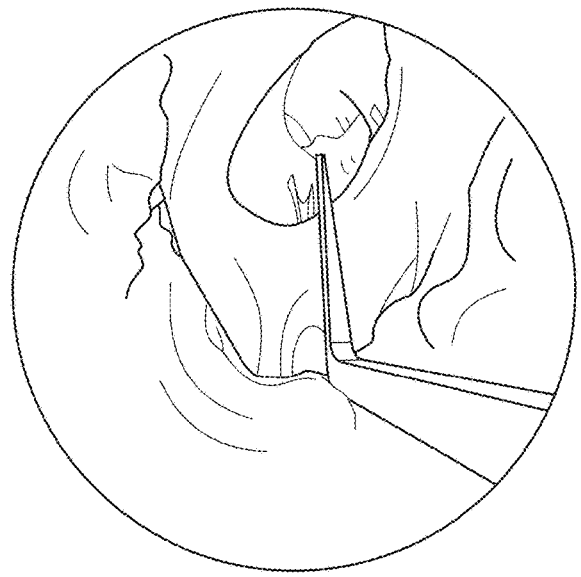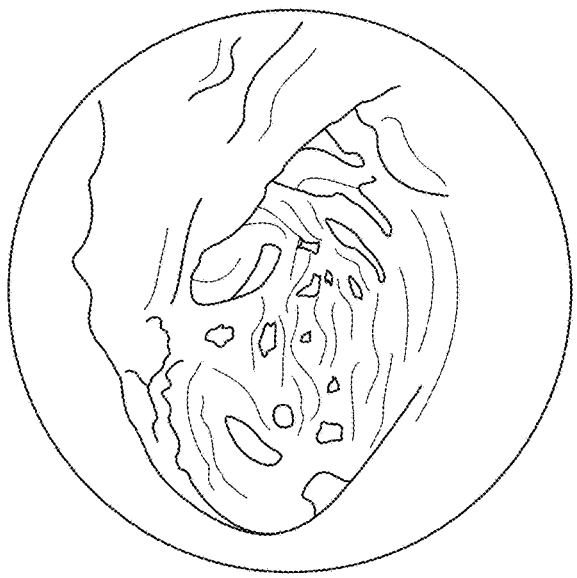
FIG. 13A  FIG. 13B
Overlay
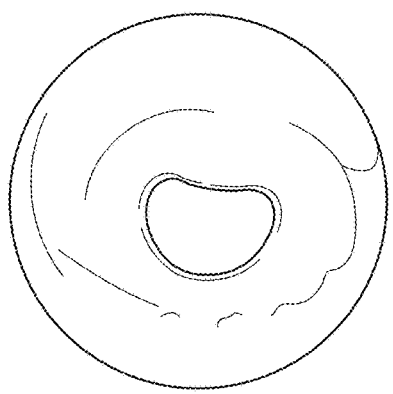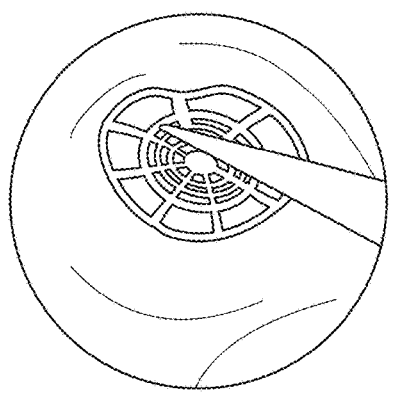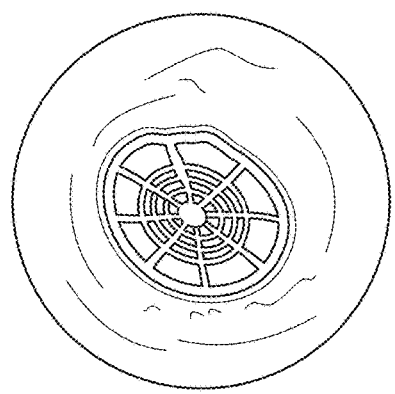
FIG. 14A  FIG. 14B  FIG. 14C

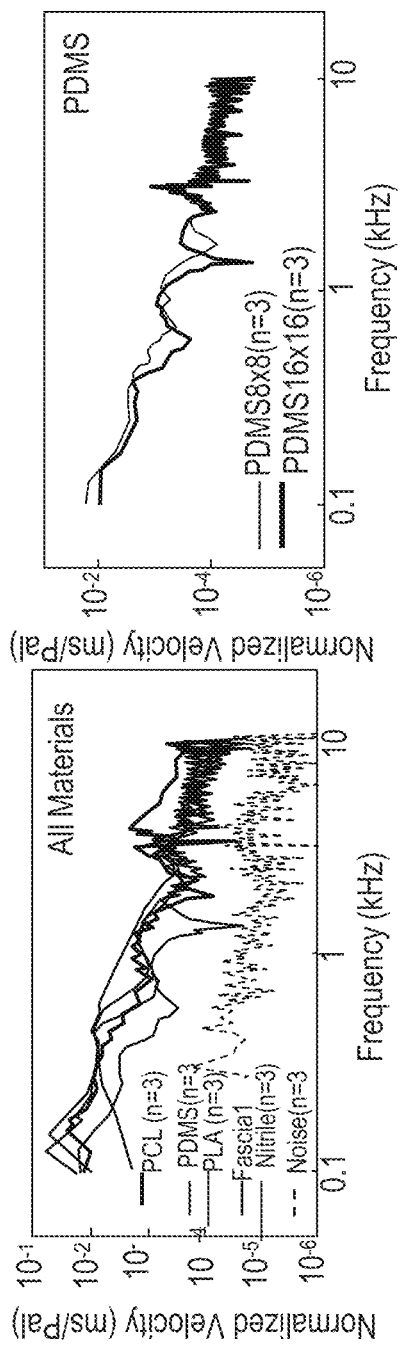
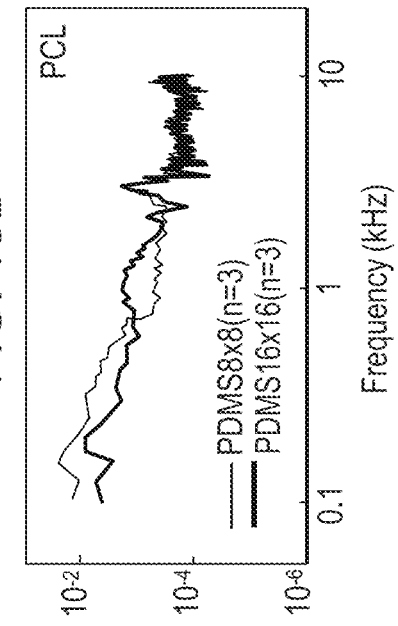
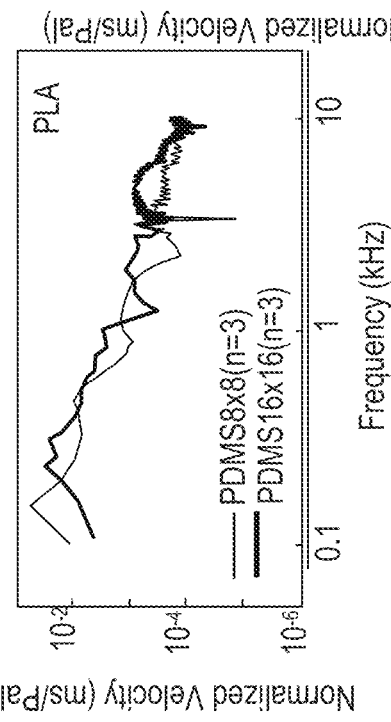

FIG. 15A
FIG. 15B
FIG. 15C
FIG. 15D

Velocity normalized by stimulus pressure of tympanic membrane composite grafts and controls across human frequency range shown. (A) Laser Doppler vibrometry measured mean velocity for TM composite grafts of varying composition (PDMS, PLA, and PCL), and fascia. Note similarities in low to mid frequencies for TM composite grafts and fascia, while nitrile has a distinctly different pattern. PLA moves with larger velocities compared to PDMS and PCL indicating notable differences in acoustic properties based on filament type. (B-D) Comparisons of PDMS, PLA and PCL-based composite grafts with different designs (*C/8R and 16C*16R). TM composite grafts of higher fiber count demonstrate slightly lower mean velocity (PCL). Despite doubling the fiber count, distinctly similar velocity patterns are seen with each print material. Noise-artifact level indicates background movement of the graft support, velocities at least a factor of 3 above the noise-artifact level are considered significant.

ARTIFICIAL TYMPANIC MEMBRANE DEVICES AND USES

CROSS-REFERENCE TO RELATED APPLICATIONS

This application is a § 371 U.S. National Phase Application of International Application No. PCT/US2016/023482, filed on Mar. 21, 2017, and claims the benefit of U.S. Application Ser. No. 62/247,268, filed on Oct. 28, 2015, U.S. Application Ser. No. 62/245,827, filed on Oct. 23, 2015 and U.S. Application Ser. No. 62/136,097, filed on Mar. 20, 2015. The entire contents of the foregoing are incorporated herein by reference.

FIELD OF THE INVENTION

The present document relates to artificial grafts.

BACKGROUND OF THE INVENTION

Three-dimensional (3D) printing is a type of additive manufacturing in which a desired 3D shape or object is built up from an available supply of material. In some cases, the material is initially a solid that is temporarily melted, a liquid that is solidified, or a powder that is solidified during the manufacturing process. Examples of 3D printing techniques include stereolithography, in which a photo-responsive resin is hardened with a laser; fused deposition modeling (FDM), in which a solid material is melted, printed, and fused to surrounding material when solidified; filamentary extrusion/direct ink writing, in which the ink is extruded from a nozzle head via pressure and the resultant object can be cured or sintered; and granular material binding, in which a bed of granular material is bound, often with heat or a fluid binder. Other 3D additive manufacturing methods include Fused Filament Fabrication (FFF), Stereolithography (SLA), Digital Light Processing (DLP), Electron-beam melting (EBM), Selective laser melting (SLM), Selective heat sintering (SHS), Selective laser sintering (SLS), Direct metal laser sintering (DMLS), Laminated object manufacturing (LOM), and Electron Beam Freeform Fabrication (EBF3).

A tympanic membrane graft is an implant or transplant used in the performance of tympanoplasty, the surgical operation performed to reconstruct and/or repair a patient's tympanic membrane. Tympanoplasty procedures may also involve reconstruction of the middle ear ossicles as they are in continuity with the tympanic membrane. Tympanic membrane grafts typically consist of autologous temporalis fascia, perichondrium, cartilage, and/or skin grafts. Tympanoplasty is often referred to as myringoplasty when only the tympanic membrane is addressed surgically.

SUMMARY

Artificial tympanic membrane devices can be constructed by preparing, for example, by 3D printing, a scaffold of ribs, and subsequently or simultaneously infilling open spaces or voids between the ribs with the same or different materials to form a membrane. Together, the scaffold and membrane form the artificial tympanic membrane device, which can then be used as a surgical graft to be implanted into subjects, e.g., human patients, with, for example, chronic otitis media—a persistent inflammation of the middle ear resulting from poor ventilation through the Eustachian tube, perforations in a patient's tympanic membrane, scarred tympanic membranes with poor mobility, or blast injuries in the military or civilian populations, chronic retraction of the tympanic membrane, as well as other clinical etiologies.

The new graft devices also can be used as in vitro tools to study tympanic membrane properties by analyzing particular structural features of the membranes and then recreating these features independently through a 3D printing platform.

Bilayer tympanic membrane graft devices, e.g., interlocking bilayer graft devices, can be prepared using similar techniques to the single-component artificial tympanic membrane devices, and can be used to repair tympanic membrane perforations, e.g., subtotal perforations. These two-component bilayer graft devices include an underlay graft device designed to adhere to the underside of the tympanic membrane facing the middle ear, and an overlay graft device that is secured on top of the tympanic membrane facing the external ear canal. One of the two graft components, e.g., the underlay graft device, includes a projection, e.g., an interlocking projection, designed and configured to fit into and extend through the perforation and interlock with an opening in the second component, e.g., the overlay graft device, to secure the bilayer graft device such that the tympanic membrane surrounding the perforation and surrounding cuff of healthy TM tissue is sandwiched between the two components (layers) of the graft device to promote wound repair and ensure proper biological environmental milieu. The opening in the overlay device and the projection in the underlay device can fit together in a so-called "lock and key" design.

In some embodiments, the two graft components can be secured by a tissue or other biocompatible adhesive, e.g., a fibrin glue, or a tether or stitch to hold the two components together. In these embodiments, there may be no projection, or each component can include a projection that passes through the perforation to meet and contact the projection from the other component (thus these projections are typically shorter and simpler in configuration than in the lock and key approach). In addition, even in the lock and key approach, an adhesive can additionally be used.

In one aspect, this disclosure features artificial tympanic membrane graft devices that include a scaffold that includes a plurality of ribs made of a first material or combination of materials, and a plurality of open spaces or voids between the ribs filled or made with the first material or combination of materials, a different, second material, a combination of the first and a second materials, or a combination of a second material and one or more other different materials, e.g., to form a thin artificial membrane between the ribs. In certain implementations, these graft devices can be used to form an underlay graft device, e.g., by connecting to a surface of the artificial tympanic membrane device a projection configured to fit through a tympanic membrane perforation, or an overlay graft device having an opening configured to fit over and lock into a corresponding projection of an underlay graft device.

Implementations of the new devices can include any combination, one, all, or none of the following features. At least some ribs of the scaffold can be formed in circular shapes and at least some ribs of the scaffold can form a radial pattern. At least some ribs of the scaffold can be formed in a hub and spoke arrangement. At least some ribs of the scaffold can be formed in a group of concentric geometric shape, e.g., a flat circular shape. The artificial tympanic membranes can be designed to form a circular conical shape or some other 3D shape, e.g., a portion of a cone. In various embodiments, the first material, e.g., a scaffold or rib material, can include one or more of polydimethylsiloxane (PDMS), hyaluronic acid (HA), poly(glycolic acid) (PGA), poly (lactic-co-glycolic acid) (PLGA), polylactic acid (PLA), polyester carbonate urethane urea (PECUU), poly octamethylene maleate anhydride citrate (POMaC), poly (glycerol sebacate) (PGS), poly(octanediol-co-citrate) (POC), polyurethane, collagen (e.g., type III collagen), fibrin, extracellular matrix, nylon, silk, poliglecaprone, and elastin. Hydrogels can also be included, e.g., in mixtures with other scaffold/rib materials already listed above.

The second material, e.g., an infill material, can include one or more of the first materials and/or one or more hydrogels and/or one or more other materials. Some examples of infill materials that can be used in the methods described herein include, but are not limited to, collagen, e.g., type III collagen, extracellular matrix, hydrogels, e.g., fibrin hydrogel, titanium dioxide, cellulose, gelatin, agarose, alginate, poly(N-isopropylacrylamide), hyaluronic acid, poly(vinyl alcohol) (PVA), poly (acrylic acid) (PAA), polycaprolactone, poly(3-hydroxybuterate-co-3-hydroxyvalerate, pluronic PLA, PGA, transglutaminase, PLGA, PDMS, poliglecaprone, polyester carbonate urethane urea (PECUU), poly octamethylene maleate anhydride citrate (POMaC), poly(glycerol sebacate) (PGS), poly(octanediol-co-citrate) (POC), polyurethane, and a mixture of collagen and fibrin. The second material can thus include mixtures of two or more of these materials, e.g., collagen and fibrin or collagen, fibrin, and a hydrogel that supports the growth of cells. These infill materials can also be used as the scaffold/rib materials, and vice versa.

The devices can further include one or more of a cellular adhesion and/or a cell invasion-inducing material, e.g., growth factors. The devices can further include one or more cells, e.g., fibroblasts, chondrocytes, keratinocytes, stem cells, progenitor cells, and epithelial cells. The cells can be harvested from the patient or from different sources, e.g., a transplant from another subject or from cultured cell lines. The growth factors can include a fibroblast growth factor (FGF), vascular endothelial growth factor (VEGF), platelet-derived growth factor (PDGF), and a keratinocyte growth factor (KGF). These growth factors can be included either directly in the entire infill or preferentially patterned during the 3D printing process to replicate native growth factor gradients or polarize sides of the tympanic membrane (TM) to promote and "tune" ingrowth of different cell types. The devices can further include one or more drug eluting materials.

In various embodiments, the devices can have a diameter of 0.5 to 12 millimeters, e.g., 1, 2, 3, 5, 7, 9, 10, or 11 mm. The devices can have a diameter based on a specific patient, e.g., a human patient. The devices can have a thickness of 10 to 750 microns, e.g., 25, 50, 75, 100, 125, 150, 175, 200, 250, 300, 400, 500, 600, or 750 microns. In some embodiments the devices are impermeable to air while in other embodiments they can be permeable to air. The devices can also be designed to be permeable to one or more drugs or other agents including small molecules, biologics, steroids, and antibiotics.

In some embodiments, the devices can include an ossicular connector on one surface of the tympanic membrane graft. The ossicular connector can be formed as an artificial umbo, malleus, or stapes and take the shape of one of an umbo, malleus, or stapes, or of a ring, a hinge, loop, archway, or a ball or socket, or some combination thereof. For example, such ossicular connectors can be secured to a surface of an artificial tympanic membrane graft devices, e.g., an underlay graft device. In various embodiments, the connector can connect to a remnant ossicular chain in the patient's middle ear or to an ossicular prosthesis implanted in the middle ear before or at the same time as the tympanic membrane graft(s) are implanted.

In another aspect, the disclosure features methods of implanting the artificial tympanic membrane devices as described herein into a patient to heal or augment a damaged tympanic membrane or to replace a missing tympanic membrane or portion thereof, e.g., to repair a perforation. The disclosure also features the use of any of the devices described herein to heal, augment, or replace a damaged or missing tympanic membrane. The methods include accessing the damaged or missing tympanic membrane; obtaining an appropriately sized and configured artificial tympanic membrane device; and securing the artificial tympanic membrane device to seal the damaged portion of the tympanic membrane or replacing the missing tympanic membrane or missing portion thereof. For example, one can repair a tympanic membrane perforation by inserting a compressed or rolled underlay graft device through the perforation and allowing the underlay graft device to unfurl and adhere to the underside of the tympanic membrane facing the middle ear, and then connecting an overlay graft device to a projection of the underlay device, at least a portion of which extends through the perforation to secure the bilayer graft device with the tympanic membrane surrounding the perforation sandwiched between the two layers of the graft device. An insertion device can also be used to place the underlay and/or the overlay graft.

In some embodiments, the projection can be secured to the overlay device, or the overlay and underlay devices can be connected or manufactured in one piece before implantation into the ear (e.g., in the shape of a "dumbbell" in which a narrow central connecting portion of the dumbbell passes through the perforation in the tympanic membrane to secure two wider flat portions on either side of the tympanic membrane).

The disclosure also features methods of fabricating one or more of the artificial tympanic membrane graft devices and the interlocking bilayer grafts devices described herein. These methods include forming a scaffold including a plurality of ribs using a first material, or combination of materials, and defining one or more open spaces between the ribs; and forming a thin membrane in the open spaces between the ribs using the first material or combination of materials, a different, second material, a combination of the first and a second materials, or a combination of the second material and one or more other different materials. Thereafter or during constructing of the first component, e.g., for an underlay graft device, a specifically shaped projection is constructed in place or is later secured to the graft device. At least a portion of the projection is configured to fit through the perforation to be repaired. For example, the projection can be T-shaped, button-shaped, or ball-shaped. While an external profile of the projection can be designed and constructed to correspond precisely to the tympanic membrane perforation, this is not required as long as the projection, or a portion of the projection, fits through the perforation. For the second component, e.g., the overlay graft devices, each is constructed or cut after construction to include an opening that corresponds to the external shape of the projection on the underlay graft device.

In another aspect, the disclosure features new bilayer tympanic membrane devices that include or consist of a pair of artificial tympanic membrane devices described herein. In these bilayer device, a first component of the pair of artificial tympanic membrane devices further comprises a projection, and wherein a second component of the pair of artificial tympanic membrane devices further comprises an opening configured to enable insertion of the projection, wherein the first component and the second component can be secured to each other. In some implementations, the opening and the projection can include or consist of a lock and key configuration, a socket and ball configuration, or an opening and hinge configuration.

The disclosure also features methods of repairing a tympanic membrane perforation and the use of the new bilayer tympanic membrane devices to repair such perforations. The methods include obtaining a bilayer tympanic membrane device as described herein; inserting the first component as an underlay graft device through the perforation and securing a surface of the underlay device to the tympanic membrane such that the projection protrudes through the perforation; applying the second component as an overlay device over the perforation such that the projection protrudes through the opening of the overlay device and extends beyond a surface of the overlay device; and moving one or both of the overlay device and the projection or underlay device with respect to each other such that a portion of the projection is securely fit onto a surface of the overlay device to lock the underlay and overlay devices together, sandwiching the tympanic membrane and perforation between them.

In these methods, a top surface of the underlay device can be adhered to the inner surface of the tympanic membrane by capillary action or adhesion, or a tissue adhesive, such as a fibrin glue. The methods can be performed in a clinical setting with or without local analgesia, and without sedation or general anesthesia. In some implementations, the methods are performed in an operating room with sedation or anesthesia.

Implementations of the new methods can include any combination, one, all, or none of the following features. The new methods of fabricating the scaffold can include printing the scaffold with a three-dimensional (3D) printer and filling the one or more voids between the ribs by filling with a second material. The 3D printer can include a nozzle for extruding the first material, wherein the nozzle can have an opening of 500 μm or less in diameter, e.g., 10 to 500, 10, 20, 30, 40, 50, 75, 100, 150, 200, 250, 300, 350, 400, or 450 μm or less in diameter. Printing the scaffold can include printing the scaffold onto a substrate that includes one or more of glass, poloxamer, polytetrafluoro-ethylene (PTFE), and metal foil, e.g., aluminum foil. Infilling the voids of the scaffold with the second material can include removing the scaffold from a substrate of the 3D printer; filling a well with the second material in a liquid form; placing the scaffold in the well with the second material; and curing the scaffold and infilled second material to solidify the second material. Curing the scaffold and infilled second material to solidify the second material includes incubating the scaffold and infilled second material in deionized water at 37° Celsius.

In some implementations, the scaffolds can be prepared using, for example, using polydimethylsiloxane (PDMS), hyaluronic acid (HA), poly(glycolic acid) (PGA), poly (lactic-co-glycolic acid) (PLGA), polylactic acid (PLA), polyester carbonate urethane urea (PECUU), poly octamethylene maleate anhydride citrate (POMaC), poly(glycerol sebacate) (PGS), poly(octanediol-co-citrate) (POC), polyurethane, elastin, collagen, e.g., spun collagen, fibrin, nylon, silk, poliglecaprone, and polymers of any one or more of these materials, e.g., hyaluronic acid polymers. The infilled second material can be any of these materials and/or can be a hydrogel, such as a bovine fibrin hydrogel.

The systems and processes described here can be used to provide a number of advantages. The new artificial tympanic membrane graft devices and interlocking bilayer graft devices can be acoustically tuned to mimic or improve upon the acoustic properties of perforated or otherwise damaged tympanic membranes, e.g., of a specific patient, or of a group of patients. In addition, the new artificial tympanic membrane graft devices can be designed to resist perforation and retraction, and to provide a robust attachment to the ossicular chain or directly to the footplate into the inner ear. These grafts can be designed to be impermeable to air or liquids or permeable to air but not liquids, and/or permeable to small molecules and/or biologics or other specific agents. In some embodiments, the graft's geometry can be designed based on the anatomical features and deficits of the particular patient for whom they are intended. The grafts can be made of materials that have equivalent or greater mechanical strength than a natural tympanic membrane or natural, tissue-based membrane graft, which can reduce the chance of perforations and/or retraction. The materials can be dimensionally stable, which can help avoid retraction, and provide for secure attachment to the ossicular chain. 3D printing technology is used to recapitulate the conical shape of a native TM or design a patch to match the curvature of the patient's TM. Conical shapes can be creating through the use of supporting molds or sacrificial materials, such as pluronic inks.

The devices can be designed with or without an ossicular connector component which, incorporated into the tympanic membrane, would allow direct attachment of the tympanic membrane to the ossicular chain or directly to the footplate of the inner ear to ensure robust coupling of acoustic energy from the tympanic membrane to the inner ear. The tympanic membrane grafts described herein can facilitate the delivery of drugs and/or air to the middle ear, thus improving and expediting wound healing, can improved conductive hearing, can decrease the need for re-operation for revision surgery, and can be customized and/or personalized to provide grafts based on a patient's size of defect and acoustic needs.

Use of the new tympanic membrane grafts can avoid the need for a second operation for hearing reconstruction. These grafts can increase the ease of surgical manipulation and can be easily handled due to being formulated to the appropriate size preoperatively. In addition, absorbable or non-absorbable materials can be used and selected based on patient-specific criteria and criteria of the surgery being performed. The new interlocking bilayer graft devices can be inserted into a patient's ear to repair a tympanic membrane perforation using either standard surgical tools to manipulate the two portions of the device or using a specialized insertion tool having the shape of a cylindrical tube that enables the graft to be easily deployed through the perforation into the middle ear. In addition, the new methods can often be conducted in a doctor's office without the need for general anesthesia and thus can, in many situations, avoid the need for surgery and hospitalization.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

FIG. 1A is a schematic view of a human tympanic membrane.

FIGS. 2E-A to 2E-D are photographic representations of tympanic membrane patch graft scaffolds of various designs.

FIGS. 3B-A to 3B-C are a series of images of tympanic membrane scaffolds composed of PDMS, PLA, and PCL filaments/ribs, respectively, with 8C (C=circumferential fiber/rib structure)/8R (R+radial fiber/rib structure) and 16C/16R filamentary architectures. The TMs in the first column of each box have a total diameter of 25 mm. The next two columns show higher magnification images, 50× with a scale bar of 1 mm and 100× with a scale bar of 500 μm, respectively.

FIG. 3B-D is an image of a representative printed scaffold highlighting the key design features.

FIGS. 3C-A and 3C-B are photographic representations of a graft device with a fractal fiber/rib structure pattern, with and without a border rib structure, respectively.

FIGS. 7A and 7B together form a flow chart of an example of a process for creating tympanic membrane grafts.

FIGS. 11B-1 and 11B-2 are three-dimensional plots that show cells that have grown on the surface of scaffolds and infill material during in vitro cell studies.

FIGS. 12A-A to 12A-G, 12B-1 to 12B-8, 12C-1A to 12C-1D, 12C-2A to 12D-2D, 12D-1A to 12D-1B, and 12D-2A to 12D-2B are photographic representations of acoustic testing devices and graphical representations of data of acoustic properties of printed tympanic membranes collected from acoustic testing.

FIGS. 13A-13B are photographic representations that show a trimmed tympanic membrane graft implanted to repair a perforation in the tympanic membrane of a sheep.

FIGS. 14A-14C are photographic representations of the use of a tympanic membrane patch graft to seal a TM perforation in a chinchilla model.

FIGS. 15A-D are a series of graphs that show results of laser Doppler vibrometry ("LDV") measurements on graft devices as described herein.

Like reference symbols in the various drawings indicate like elements

DETAILED DESCRIPTION

Figure 1B:
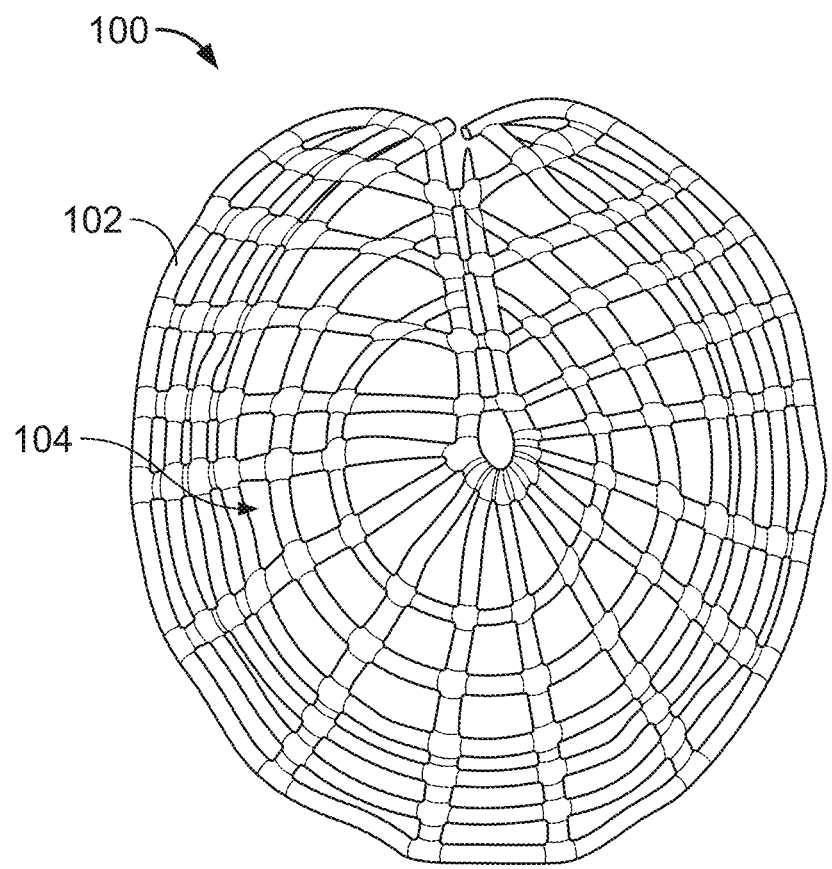
FIG. 1B is a top view of an example of a tympanic membrane graft device.

Artificial tympanic membrane devices and interlocking bilayer graft devices are described, along with some processes for manufacturing such membrane devices, uses of such membrane devices, and the results of tests performed on such membrane devices.

To specifically address partial tympanic membrane perforations (which represent the majority of perforations seen in clinical practice), we have devised a bilayer, interlocking TM graft to facilitate perforation repair. The graft may potentially be used in the clinic setting, thereby avoiding general anesthesia and surgery-related morbidity, such as from post-auricular or transcanal soft tissue incisions. Alternatively, the graft may be used in an operating room setting with sedation or anesthesia, if required in specific situations. Placed through the ear canal, the new graft devices provide the advantages of surgical tympanoplasty without the need for an operation. The bilayer design allows for a combination underlay and overlay graft approach using scaffold fiber arrangements with favorable acoustic and resilient mechanical properties. Unlike "patch" approaches to TM repair, this "sandwich" bilayer design grafts components to both the outer ear and inner ear surfaces of the TM, providing an ideal environment for cellular migration and proliferation and healing of the TM after injury. 3D printing can be used to produce the new key/lock devices to ensure stability of the graft, even in the face of positive or negative middle ear pressure. However, other types of features may be used instead of the lock and key. For example, a ball and socket, hinge, tether, stitch, and/or adhesive may be used.

Tympanic Membrane Graft Devices

Artificial tympanic membrane graft devices, or simply "grafts," as described herein are designed to be acoustically tuned (i.e., modified to the extent that the acoustic properties are adjusted for best sound conduction in a specific patient), resistant to perforation and retraction, and to provide a robust attachment to the ossicular chain. The artificial tympanic membrane grafts can have a scaffold, e.g., in a 2D or 3D layer, made of ribs, with voids between the ribs. An infill material, e.g., a hydrogel, is typically used to fill the voids and to create a solid, optionally semipermeable, artificial tympanic membrane graft. These artificial tympanic membrane grafts can be used as implants to repair, replace, or patch a patient's tympanic membrane. Similarly, the interlocking bilayer grafts can be used to seal tympanic membrane perforations.

In some embodiments, the artificial grafts, e.g., an interlocking bilayer grafts, are implanted without any living cells present, but includes agents that will induce cells from the patient's ear canal to migrate and colonize the graft within a time period of several weeks to months. In other embodiments, the scaffold and infill materials are used as a substrate for living cells, e.g., harvested from the patient or from other subjects, to cover or be integrated within all or part of the scaffold and/or infill materials.

FIG. 1A is a prior art schematic view of a human tympanic membrane. Inspiration for the circular and radial rib structure of the 3D printed tympanic membranes was derived from the fiber arrangement in the natural tympanic membrane. Circular and radial fibers along with a malleus region were traced using a Visual G-code program. The drawing was converted into a G-code program that was 3D printed via filamentary extrusion of SE1700 polydimethylsiloxane (PDMS).

In some embodiments the artificial tympanic membrane grafts and the two layers and projection of the bilayer grafts can be manufactured by first "printing" the scaffold using a 3D printer that dispenses a biocompatible "ink." Once solidified and removed from the 3D printer's printing surface, the scaffold can be submerged in a curable liquid. This liquid can fill the voids between ribs of the scaffold, and then be cured to form a solid membrane between the ribs of the scaffold. Once cured, the artificial tympanic membrane graft can be used in tympanoplasty and/or myringoplasty operations for the reconstruction of a patient's tympanic membrane. In addition, the bilayer grafts can be used to simply and effectively repair tympanic membrane perforations.

In other embodiments the artificial tympanic membrane grafts and bilayer grafts can be manufactured by printing the scaffold and the infill material simultaneously or serially using a 3D printer that dispenses one or more types of biocompatible inks. The ribs and infill material may consist of two different printed materials, or in some circumstances may consist of different patterns of the same material. Once manufacture is complete, the graft is removed from the 3D printer's printing surface and cured by one or more methods, which may include for example, heat curing, curing by UV light, carbon dioxide or other gas, pressure, or cooling. This material may have other useful properties, such as being absorbable or non-absorbable, permeable or non-permeable, drug eluting, cellularized, etc.

FIG. 1B is a top view of a schematic of an artificial tympanic membrane graft 100. The shape of the tympanic membrane graft 100 may be generally circular, with a center that may be elevated or flat to create an overall shape that is, or that approaches, a circular, flat, or conical construct. The tympanic membrane graft 100 includes ribs 102 and voids 104 filled with an infill material. This arrangement of ribs allows for a biomimetic architecture that may allow the 3D printed tympanic membranes to have similar or improved acoustic and mechanic properties to the native tympanic membrane.

The overall size and shape of the tympanic membrane graft 100 may be selected based on the patient for which the tympanic membrane graft 100 is created. For example, for an adult human, the tympanic membrane graft 100 may be created with a diameter on the order of a few millimeters. For example, the diameter of the tympanic membrane graft 100 can be about 0.5, 1, 2, 3, 5, 8, 10, 12, 14, 16, 17, 18, or 19 millimeters, or more or less as is technologically and physiologically appropriate. For example, smaller sizes may be appropriate to patch a tympanic membrane while larger sizes may be appropriate when used to completely replace a tympanic membrane.

The size and shape of the bilayer grafts will depend on the size of the overall tympanic membrane of the patient, but more importantly based on the size of the perforation. Both the underlay graft and the overlay graft should be at least about 1 to 2 mm larger in size than the greatest dimension of the perforation. In addition, the projection on the underlay (or overlay) can be a host of different shapes and sizes to facilitate placement.

Scaffolds

Figure 2A:
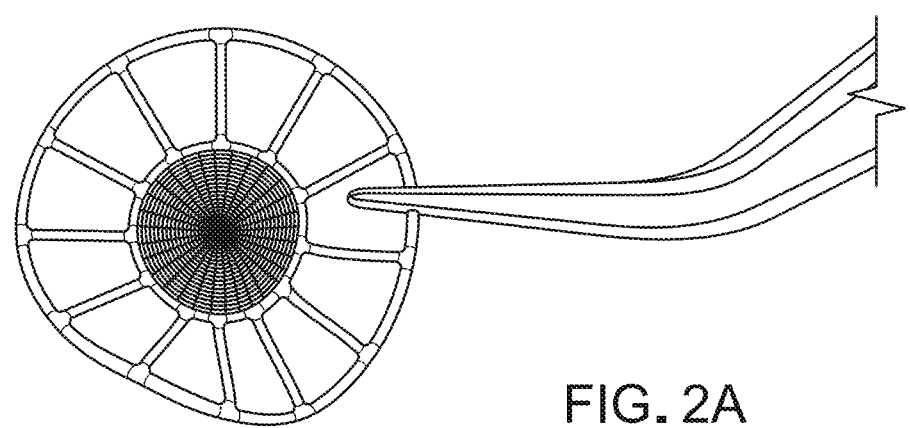
FIGS. 2A and 2B are views of examples of scaffolds of a tympanic membrane graft including a ring connector (as shown in FIG. 2B).
Figure 2B:
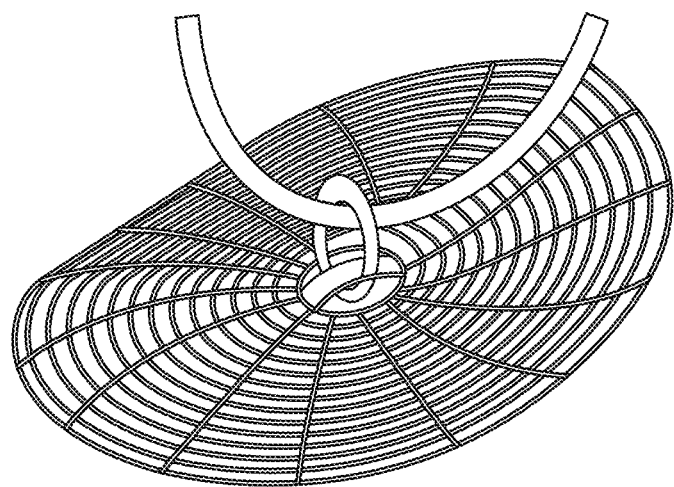

FIGS. 2A and 2B are views of examples of scaffolds of tympanic membrane grafts. The views shown were created from a photograph of the scaffold taken before all of the infill material was added to fill voids of the scaffold.

The scaffold includes many ribs. Some of the ribs of the scaffold are formed in circular, or nearly circular, shapes. In addition, some of the ribs of the scaffold are formed in straight, or nearly straight shapes arranged in a radial pattern. Alternatively, some of the ribs of the scaffold may be described as forming a hub and spoke arrangement, while some other ribs of the scaffold are formed in a group of concentric geometric shapes.

Between the ribs of the scaffold are voids. The voids are areas without any material of the scaffold. Infill materials are used to fill the voids, as will be discussed below. In some embodiments, the same material as used for the ribs, or a different material, can also be used to 3D print a thin sheet of material to fill the voids.

Figure 2C:
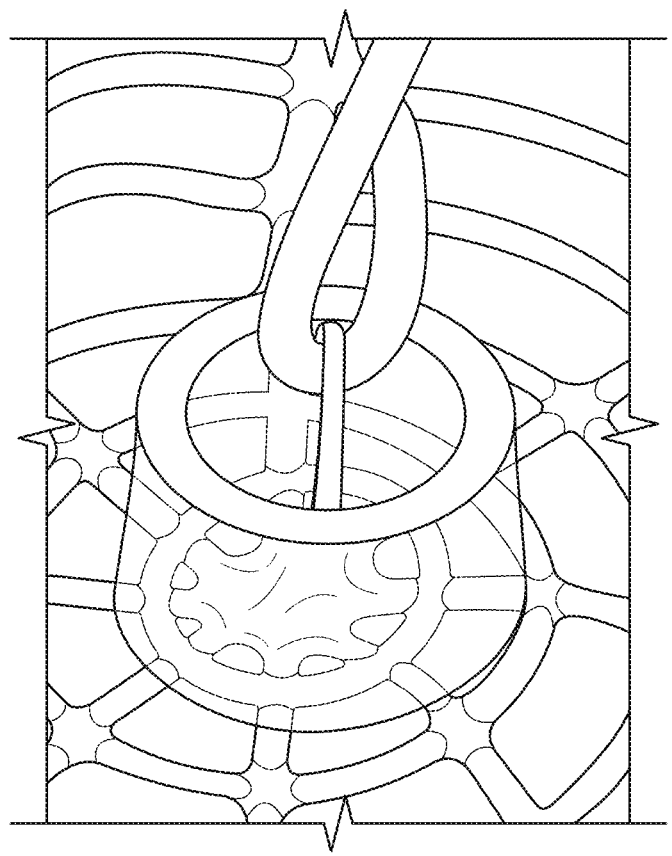
FIG. 2C is a photographic representation of an example of an ossicular connector on the surface of a tympanic membrane graft device scaffold that has a single arch ring connector design for attachment to the ossicular chain.
Figure 2D:
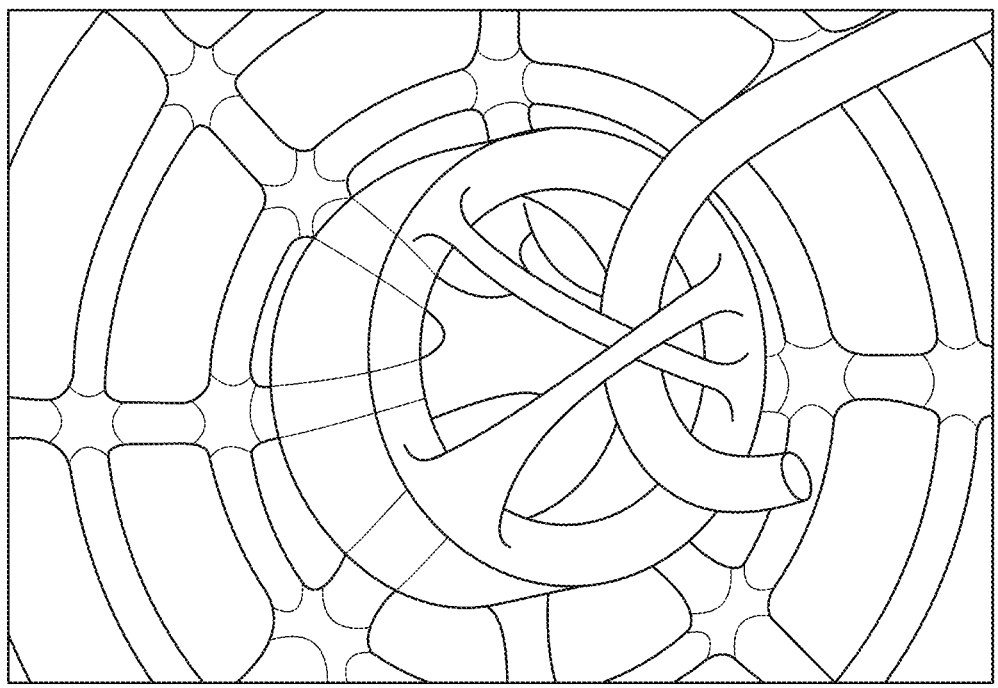
FIG. 2D is a photographic representation of an example of an ossicular connector on the surface of a tympanic membrane graft device scaffold that has a double arch ring connector design for attachment to the ossicular chain.

The cross-sectional shape of the ribs may be any technologically appropriate shape, including but not limited to circular, rectangular (e.g., square), triangular, or irregular. The diameter or thickness (at the widest point) of the ribs may be on the order of tens to hundreds of microns. For example, the thickness of the individual ribs may be from 5 to 50 microns up to 500 to 800 microns, e.g., 10 to 100 microns, 100 to 500 microns, or 5, 10, 25, 50, 75, 100, 125, 150, 175, 200, 225, 250, 275, 300, 325, 350, 375, 400, 425, 450, 475, 500, 550, 600, 650, 700 750, or 800 microns, or more or less as is technologically and physiologically appropriate. The ribs can also be shaped to form an ossicular connector to enable connection of the tympanic membrane graft to the malleus, incus, or stapes, or to a remnant of one of the ossicles, or to a commercially available existing prosthesis, or directly to the inner ear, e.g., to the footplate of the oval window. The connector may replace the ossicular chain in entirety or one component of it. This connector can be made of the same or a different material, e.g., hydroxyapatite, titanium, or nitinol, from the material used for the rest of the scaffold. As shown in FIGS. 2B to 2D, the connector may take the shape of a ball and socket, snap, hinge, circular aperture, or different connecting configuration that would attach an integrated component from the tympanic membrane to the native or synthetic ossicle(s).

FIG. 2A shows an example of a scaffold with additional material beyond the circumference of the scaffold. The additional material may be the same or different material from the graft scaffold and infill, and may serve as means to secure the graft for in vitro testing, or for mounting in the eardrum to the ear canal in live surgery. The central region is the scaffold, surrounded by radially extending ribs. Voids between the ribs can be filled with infill material.

FIG. 2B shows an example of a scaffold with additional material to function as a connector region to attach the graft to ossicular prostheses. A printed scaffold with a connector loop enables an ossicular prosthesis to be crimped onto the tympanic membrane graft to create a solid connection between the tympanic membrane graft and the ossicular chain or oval window. FIG. 2C is a photo of an example of an ossicular connector on the surface of a tympanic membrane graft device scaffold that has a single arch ring connector design for attachment to the ossicular chain. FIG. 2D is a photo of an example of an ossicular connector on the surface of a tympanic membrane graft device scaffold that has a double arch ring connector design for attachment to the ossicular chain.

FIGS. 2E-A to 2E-D are photographic representations of tympanic membrane patch graft scaffolds of various designs referred to herein as tunable arc patches that include arc fibers (A), radial fibers (R) and a border region around the outside of the device. These patches can be used individually or as part of the bilayer devices described herein. Each of these elements of the device can be designed (i.e., "tuned") to meet specific needs of a particular patient.

Figure 3A:
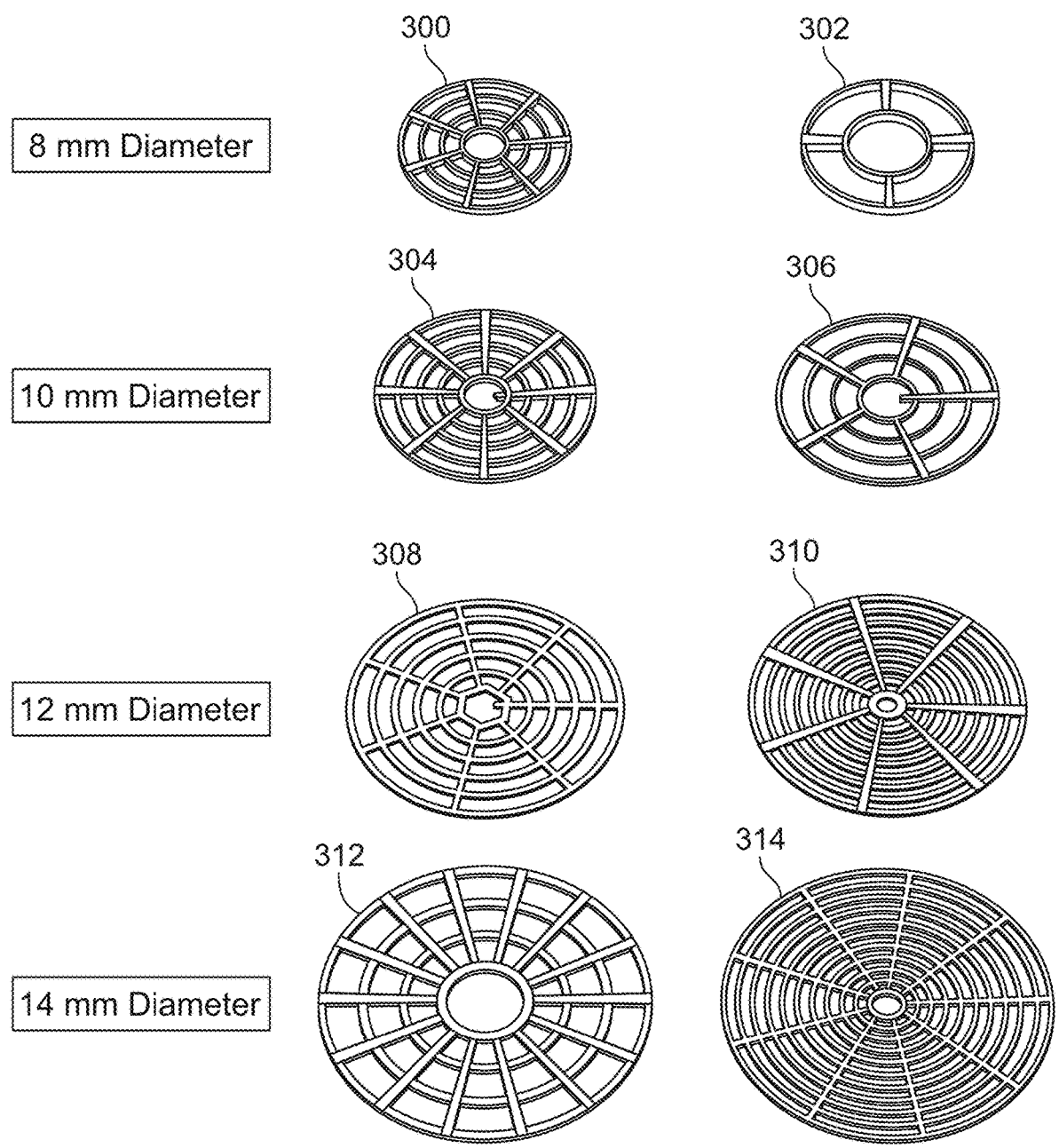
FIG. 3A is a view of examples of scaffolds of varying sizes and geometries.

FIG. 3A is a view of several examples of different scaffolds 300-314 of varying sizes and geometries. As shown, scaffolds can be created with varying overall diameters, including diameters ranging from 8 mm to 14 mm. However, larger and/or smaller diameters are possible, depending on a particular patient's needs. Each of the scaffolds 300-314 include ribs, and each of the scaffolds 300-314 include a different number of ribs and voids arranged in different configurations. FIGS. 3B-A to 3B-C show other scaffolds with differing numbers and arrangements of radial fibers (R) circumferential fibers (C) and a border region fiber manufactured polydimethylsiloxane (PDMS), hyaluronic acid (HA), poly(glycolic acid) (PGA), poly (lactic-co-glycolic acid) (PLGA), polylactic acid (PLA), polyester carbonate urethane urea (PECUU), poly octamethylene maleate anhydride citrate (POMaC), poly (glycerol sebacate) (PGS), poly(octanediol-co-citrate) (POC), and/or polyurethane. FIG. 3B-D shows the basic format.

The underlay graft devices and overlay graft devices can be manufactured in the range of about 2 to 8 mm, or larger, as required to repair a particular perforation. These devices are typically about 100 to 300 microns thick, e.g., about 150 to 250 microns, e.g., 200 microns, thick.

In addition to those shown, other arrangements of ribs are possible, including non-regular or regular geometric arrangements. As each of the scaffolds 300-314 has a different number and arrangement of ribs, each of the scaffolds 300-314 has voids of different sizes, shapes, and aggregate sizes. That is, the sum total volume of voids between any two scaffolds (including those not shown) need not be the same. As will be described later, these tympanic membrane grafts can be designed for use for different patients, including different patients of different species. As such, the size of the scaffold, and thus the final tympanic membrane graft, can be selected based on the patient that will receive the graft.

Scaffolds can be created from any technologically appropriate material. For example, the material used may be selected to be biocompatible, capable of being manufactured to the size at which the scaffold is designed, and possessing the necessary mechanical properties to facilitate the transmission of vibrations to the patient once implanted. Some examples of materials that can be used in the methods described herein include, but are not limited to, polydimethylsiloxane (PDMS) (which is non-absorbable by the body), hyaluronic acid (HA), poly(glycolic acid) (PGA), poly (lactic-co-glycolic acid) (PLGA), polylactic acid (PLA) (which is absorbable), poly(glycerol sebacate) (PGS) (e.g., REGENEREZ®—a tunable, bioresorbable elastomer made of PGS with elastomeric properties), polyurethane, polyvinyl alcohol (PVA), nylon, silk, poliglecaprone, polycaprolactone (PCL) (which is absorbable by the body), polyester carbonate urethane urea (PECUU), poly octamethylene maleate anhydride citrate (POMaC), poly(octanediol-co-citrate) (POC), collagen, fibrin, and elastin.

The scaffold can also be plasma treated to enhance adhesion of the infill materials and enhance cellular binding capabilities. Plasma treatment cleans the samples and also puts hydrophilic groups on the surfaces so that biologic materials, such as collagen and fibrin, can adhere more readily. Other treatment of scaffolds may include application of substances that improve cellular adhesion including oxidation, treatment with poly-D-lysine, 3-aminopropyl triethoxysilane (APTES), and cross-linking with glutaraldehyde (GA). In some cases, the scaffold may be drug eluting. For example, drugs such as β-fibroblast growth factor (FGF-β), ciprofloxacin, and dexamethasone can be delivered using the new graft devices.

These same types of scaffolds can be used to create the new bilayer graft devices, with some modifications to produce a projection on the underlay graft device and a corresponding opening or aperture in the overlay graft device. The projection is created from the same or different scaffold material as the ribs, and can be manufactured at the same time the ribs are produced or can be manufactured separately and then secured to the surface of the scaffold for the underlay device. Similarly, the opening in the overlay device can be created while the scaffold is being laid down, or can be cut out of the overlay device once the scaffold is completed, similar to one of the transmembrane graft devices described herein.

In general, the fiber and/or rib arrangements can contain 2 to 8 or more arrangements to create a mechanically stiffened and resilient structure. For example, 4 circular rib structures, 4 radial rib structures to 8 circular rib structures, and 8 radial rib structures. These arrangements can also form other patterns such as hexagonal or fractal designs to facilitate cell growth, e.g., as shown in FIGS. 3C-A and 3C-B. Such fractal designs can include repeating patterns, branching ribs, or snowflake-like patterns.

The dimensions of the bilayer graft devices can be in the range of 2-8 mm in diameter×200 microns in thickness for both the overlay and underlay graft devices, and the projection ("key") on the underlay device can be about 200 microns×1 mm.

Figure 4A:
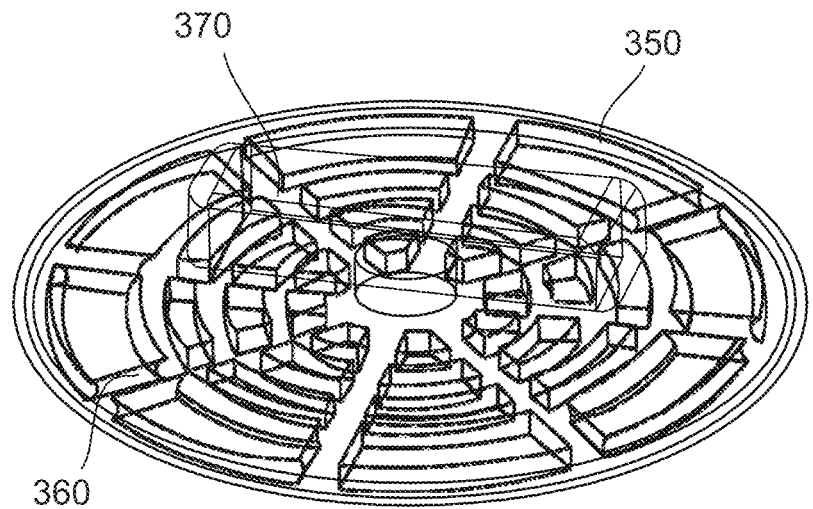
FIGS. 4A and 4B are schematic figures of an underlay graft device and an overlay graft device, respectively.
Figure 4B:
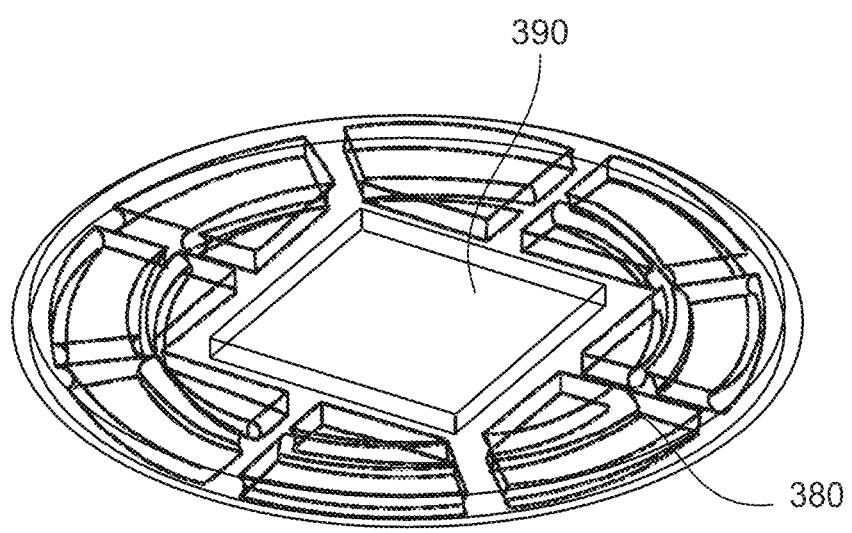

As shown in FIG. 4A, the underlay device 350 can have a scaffold 360 and a projection 370, which can have the shape of a shallow "T" in which the short base of the "T" is part of or is secured to the scaffold material 360, e.g., to the ribs, e.g., in the center of a circular underlay graft device 250, and extends upwards a distance that is about the same size or slightly larger than the thickness of the overlay graft device 380 (shown in FIG. 4B). The top of the "T" extends perpendicularly from the base, and the length of the top is about the same size or slightly smaller than the largest dimension of the opening in the overlay device. In general, to accommodate the "T"-shaped projection, as shown in FIG. 4B, the opening 390 in the overlay device 380 is generally rectangular, e.g., square, in shape and has the same general dimensions as a top view of the top of the "T," so that the top of the T-shaped projection 370 can easily pass through the opening 380, but can pass over a top surface of the overlay graft device 380 when the overlay is turned with respect to the underlay deice 350, to secure the overlay device to the underlay device in a so-called "lock and key" manner. Of course, the projection 370 can have other shapes and the opening 390 can have a corresponding shape so that together the two function in a lock and key manner.

Other types of projections and "lock and "key" type mechanisms include a button-shaped design, a hook and loop system, a ball and socket, a deployable umbrella, and a snap mechanism.

Infill Materials

One or more materials can be used to fill the voids of the scaffold of a tympanic membrane graft device or bilayer graft device, and they can be added to the scaffold using a variety of techniques. This infill material or combination of materials can, for example, determine the permeability or impermeability of the graft. The material may also include therapeutic or drug eluting materials (for the same or different drugs as used in or on the scaffold material), and can determine the surface characteristics (e.g., texture) and other physical characteristics of the graft. In some cases, the material used to infill the voids is the same as, or includes, some or all of the material used to create the scaffold. In addition, the infill materials can be added to the scaffold in a separate step, or can be deposited in the same step as the deposition of the ribs of the scaffold. For example, a 3D printer can be programmed to deposit the ribs and infill materials in one step, and the materials used for the scaffold and the infill material (membrane between the ribs) can be the same or different materials, because 3D printers can print one, two, or more different materials at the same time.

Figure 5A:
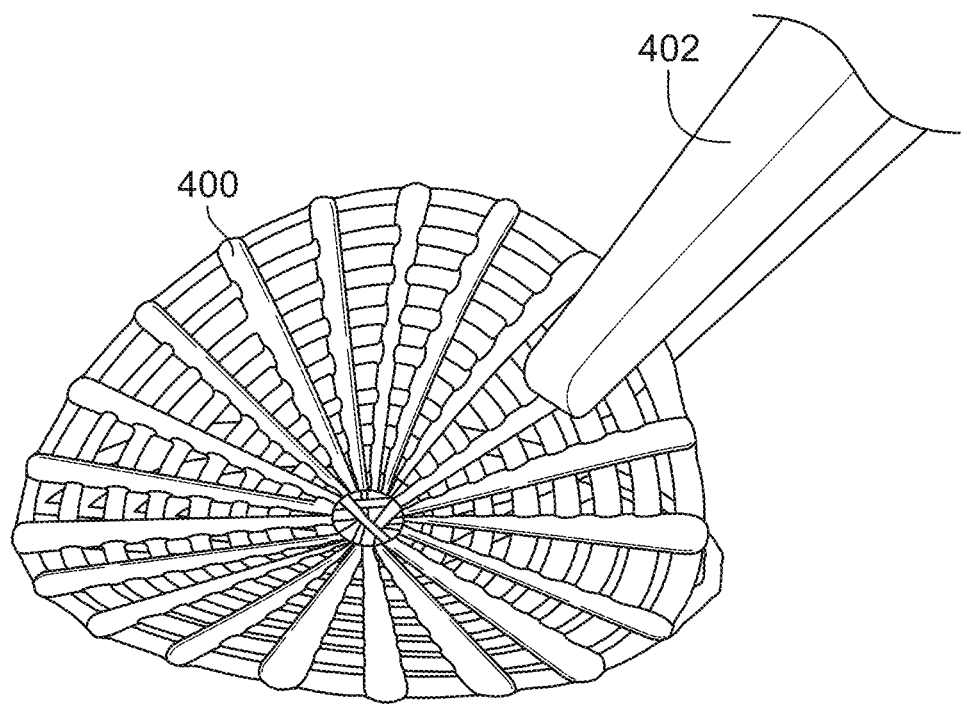
FIGS. 5A and 5B are examples of a scaffold of a tympanic membrane grafts.
Figure 5B:
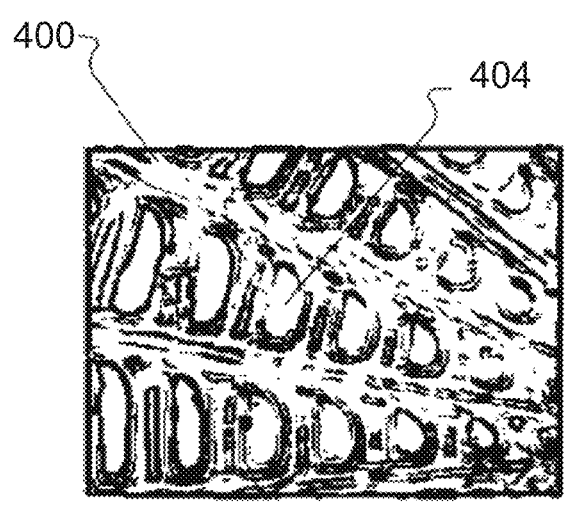

FIGS. 5A and 5B are schematics of infilling a scaffold of a tympanic membrane graft. In FIG. 5A, a semi-flat, cone-shaped scaffold 400 is removed from a printing substrate by a pair of hemostats or forceps 402 and is moved into a well containing infill material 404 shown in FIG. 5B. In addition to hemostats or forceps 402, any sort of manipulators can be used, including, but not limited to, human operated manipulators and robotic manipulators working under direct human control or working in an automated manner. In FIG. 5B, the infill material 404 has filled the voids of the scaffold 400 and solidified.

Figures 6A, 6B, 6C:
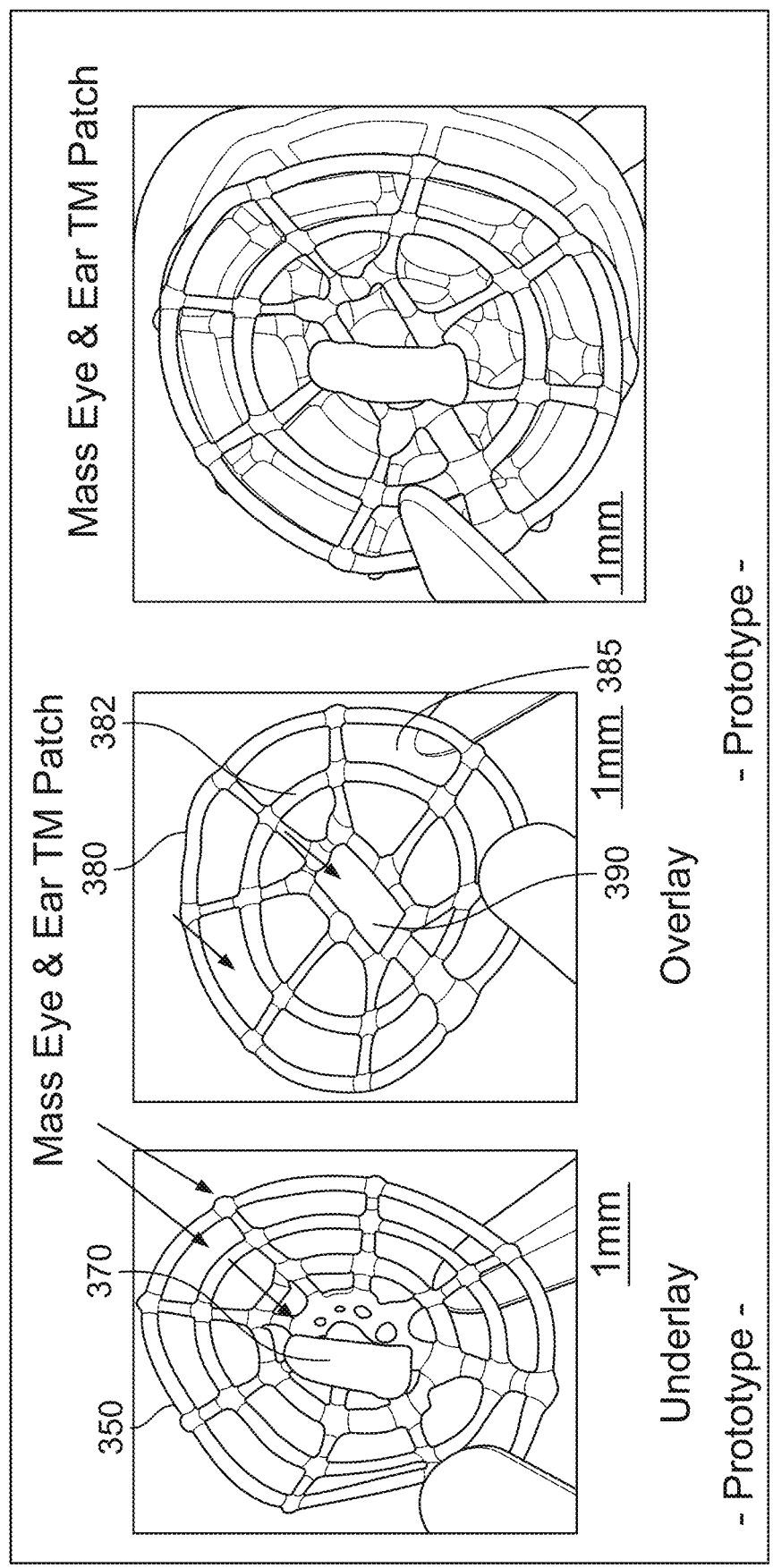
FIGS. 6A and 6B are photographic representations of an underlay graft device and an overlay graft device, respectively, showing a scaffold and infill material.
FIG. 6C is a photographic representation of a combined bilayer graft device, in which the projection of the underlay of FIG. 6A is pulled through the opening in the overlay device of FIG. 6B, and the overlay device is rotated to wedge the top or "arms" of the T-shaped projection over the surface of the overlay device, thereby securing the two together.

FIG. 6A shows an underlay graft device 350 with a rectangular T-shaped projection 370. FIG. 6B shows an overlay graft device 380 with ribs 382 and clearly shows infill material 385 between the ribs. Opening 390 is clear of the infill material. As shown in FIG. 6C, the projection 370 has been inserted or pulled through the opening 390 in the overlay device 380, and the overlay device has then been rotated so that projection 370 is securely fit over the opening 390 to secure the overlay device to the underlay device.

The infill material 385, 404 may include any technologically appropriate material. For example, the material can be selected to be biocompatible, capable of filling voids in a scaffold, and possessing the necessary mechanical properties to facilitate the transmission of vibrations to the patient once implanted. The material used can include some or all of the materials used in printing scaffolds. Some examples of infill materials that can be used in the methods described herein include, but are not limited to, collagen, e.g., type III collagen, extracellular matrix, hydrogels, e.g., fibrin hydrogel, titanium dioxide, cellulose, gelatin, agarose, alginate, poly(N-isopropylacrylamide), hyaluronic acid, poly(vinyl alcohol), poly (acrylic acid), polycaprolactone, poly(3-hydroxyburetate-co-3-hydroxyvalerate, pluronic PLA, PGA, transglutaminase, PLGA, PDMS, poliglecaprone, polyester carbonate urethane urea (PECUU), poly octamethylene maleate anhydride citrate (POMaC), poly(glycerol sebacate), poly(octanediol-co-citrate) (POC), polyurethane, and a mixture of collagen and fibrin. These materials can be used individually or in combinations of two of more different materials.

In some embodiments, the infill material can include a cellular adhesion and invasion material. For example, such materials can be included to encourage a patient's tissues in the ear canal and/or middle ear to adhere to and grow over the tympanic membrane graft after implantation, or to cover the graft with cells before implantation. Examples of such cellular adhesion and invasion material include, but are not limited to, growth factors such as one or more of a fibroblast growth factor (FGF), a vascular endothelial growth factor (VEGF), platelet-derived growth factor (PDGF), transforming growth factor beta, interleukin-4, or other factors with similar biologic properties.

Additionally, the infill material can include, or be coated with in a separate step, cellular materials. For example, such cellular materials can include, but are not limited to, one or more of fibroblasts, chondrocytes, keratinocytes, and epithelial cells. These cells can be harvested from the patient who is to receive the implant or from a relative of the patient, or from a human subject unrelated to the patient who is to receive the implant.

In addition, the infill material can include, or be coated with in a separate step, one or more drug eluting materials. For example, such drug eluting materials can be included to deliver drugs to the tissue at the graft site. Examples of such drug eluting materials include polymers that allow tuned drug elution such as polyethylene vinyl acetate (PEVA), poly n-butyl methacrylate (PBMA), Polycaprolactone (PCL), Ethylene-vinyl acetate (EVA), Polylactic acid (PLA), Poly(3-hydroxybutyrate-co-3-hydroxyvalerate (PHBV), phosphorycholine, and fluropolymer. Polymers with drugs can be printed, spray coated and/or dip coated. In some cases, one to three or more layers can be used in the coating and the dose may therefore be tailored The drugs to be eluted include, but are not limited to steroids, antibiotics, bisphosphonates, non-steroidal anti-inflammatory/immunomodulating drugs, e.g. biologics, TNF inhibitors, IL-6 inhibitor, IL-1 inhibitor, T cell mediators, antibodies that target inflammatory cells, e.g. B cells and cellular adhesion molecules, methotrexate, and cyclosporine.

Methods of Making the Artificial Tympanic Membrane Grafts

In general, creation or manufacture of a tympanic membrane graft device or bilayer graft device as described herein can include creation of one or more scaffolds, followed by infilling the voids of the scaffold with an infill material. In some cases, the infill material begins as a liquid and is then set. Additional steps, or a different order of steps, may be used as technologically appropriate. For example, different steps can be used to manufacture the graft (e.g., alternative order or types of manufacturing), and additional steps may be performed once the graft is created (e.g., sanitizing, testing, packaging). For example, the final artificial tympanic membrane grafts can be sterilized using radiation, including ultraviolet radiation, oxidization, or chemical sterilization.

For example, any one or more of the following sterilants can be used, depending on the nature of the materials used for the scaffold and infill material: ethylene oxide, ozone, bleach, glutaraldehyde and/or formaldehyde, phthaldehyde, hydrogen peroxide, peracetic acid, or silver. Some of these materials, e.g., silver, can also be incorporated into the scaffold and/or infill material during manufacture. Of course, if an artificial graft is to be covered with living cells, it would be sterilized before the living cells are added to colonize the graft.

Described below is one possible process for manufacturing a tympanic membrane graft. In this process, a scaffold is printed with a 3D printer, and the scaffold is submerged in a liquid curable infill material after the scaffold is printed. In a different process, the scaffold and the infill material are both printed by the same or two different 3D printers.

In yet another process, a scaffold is created by casting a first material in a first mold, and the scaffold voids are filled by 3D printing, use of a curable liquid material, or using a second casting with a second material or combination of materials together with the scaffold in a second mold. Other methods are possible.

Figure 7A:
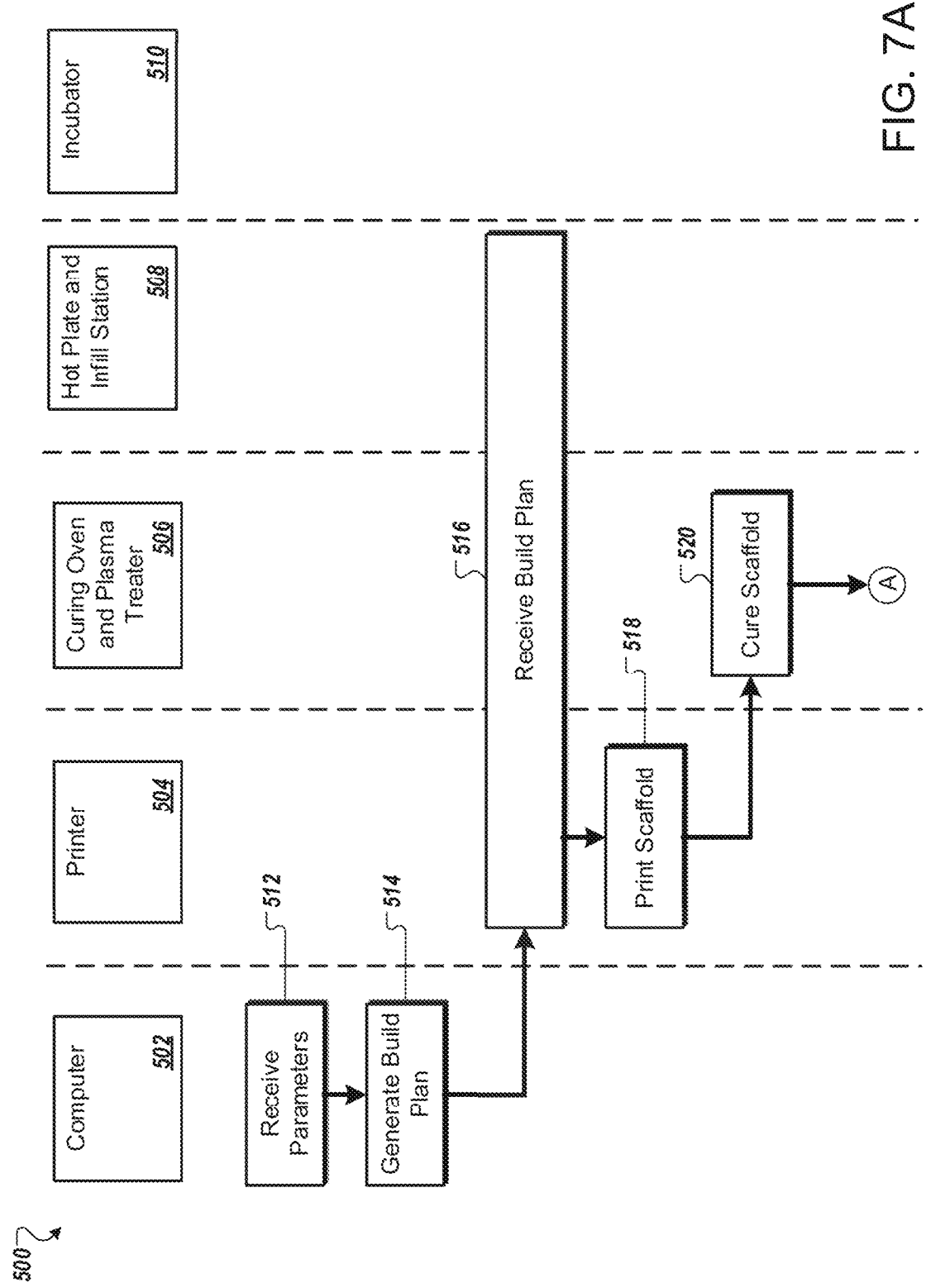

FIGS. 7A and 7B together form a flow chart diagram of an example of a process 500 for creating a tympanic membrane graft device or a bilayer graft device by printing a scaffold with a 3D printer, and the scaffold is subsequently submerged in a liquid, curable infill material after the scaffold is printed. For clarity, process 500 is being described with a particular set of machines serviced by autonomous material handling robots. However, different machines and different material handling systems, including human operators, may be used to perform the process 500 or a similar process. Similarly, the example discusses creation of a single tympanic membrane graft for clarity. However, some configurations may be used to create many tympanic membrane grafts at once, either identical copies or different, e.g., personalized, copies having different properties.

A computer 502 is used to control the 3D printer and associated equipment. Computer 502 can be a general-purpose computer such as a desktop or server computer. The computer 502 includes software to create manufacturing instructions for other elements of the system shown in FIGS. 7A and 7B. Printer 504 is a 3D printer capable of printing one or more scaffolds based on manufacturing instructions received from the computer 502. A curing oven and plasma treater 506 is a machine capable of curing a printed scaffold and/or applying a plasma treatment to the printed scaffold. A hot plate and infill station 508 is a machine that provides a temperature controlled environment in which a scaffold can be infilled. An incubator 510 is a machine that can hold a tympanic membrane graft in a temperature controlled environment.

The computer 502 can receive parameters 512 for the manufacture of one or more tympanic membrane grafts. For example, a user can enter parameters for a particular patient, including the patient's age, measurements made of the patient's ear canal and middle ear anatomy, medical imaging of the patient's anatomy, and/or a prescription for the patient, etc. Additionally or alternatively, the user can enter parameters desired of the tympanic membrane graft itself. For example, the user may enter a desired diameter; number of layers, thickness; scaffold design; and/or drug, growth factors, and/or cellular adhesion and invasion materials. In some configurations, the computer 502 may receive some or all of the parameters from a network-connected data source such as a purchasing or ordering computer, from electronic medical records, or from another appropriate data source.

From the parameters, the computer 502 can generate a build plan 514 for the desired tympanic membrane graft. The build plan 514 may include, for example, machine instructions for machines involved in the tympanic membrane graft's creation, instructions for a human operator, packaging and labeling information, etc.

In one example, to create instructions for the printer 504, a 3D scaffold model may be selected from a library of 3D scaffold models. The selected model may be picked based on, for example, fitting the size and shape specified in the parameters. Additionally or alternatively, a 3D scaffold model may be modified, for example by scaling up or down, changing rib thickness, deepening or making more shallow the 3D conical shape of the membrane, etc. The 3D model selected or created for this build may then be converted into 3D printer instructions that, when executed by the printer 504, cause the printer 504 to print the desired scaffold.

In one example, to create instructions for the curing oven and plasma treater 506, a curing time, curing temperature, and plasma treatment parameters can be looked up or calculated based on, for example, the geometry of the scaffold, the material used to print the scaffold, and other appropriate data.

In one example, to create instructions for the hot plate and fill station 508, the computer 502 can select one or more materials for use as infill material. The infill materials may be picked based on, for example, the size and geometry of the voids in the scaffold; desired surface characteristics; and/or desired drug, growth factors, and/or cellular adhesion and invasion material. The build plan may list these material, along with, for example, volumetric measures or ratios of each material and an order for which they should be added to a well.

In one example, to create instructions for the incubator 510, the computer 502 can specify environmental factors needed to incubate a tympanic membrane graft. For example, if the infill material is cured in an oven at 80° Celsius, the infill is crosslinked/gelled on a 37° Celsius hot plate. After a period of about 20 minutes, they are transferred to a deionized water bath and placed in an incubator at 37° Celsius. In another example where the infill material is photo-curable, the build plan can include instructions to hold the tympanic membrane graft under an artificial light source at the proper temperature and for a specified length of time.

In one example, to create instructions for an automated material handling device, the computer 502 can specify an order of build operations and/or a time required for each build operations. The build plan can include instructions to, for example, wait until a signal is received from the printer 504 before retrieving the scaffold from the printer 504. The build plan can also include instructions to, for example, wait a specified period of time before retrieving the tympanic membrane graft from the curing station 508.

The printer 504, curing oven and plasma treater 506, hot plate and infill station 508, and incubator 510 receive 516 the build plan. For example, the computer 502 can transmit, over a data network either wired or wirelessly, the build plan, or a portion thereof according to the receiving machine, to the other machines in the manufacturing system. Additionally or alternatively, information about the build plan may be output to a user device, for example, to allow a technician to approve, monitor, and/or participate in the manufacturing process.

Figure 8A:
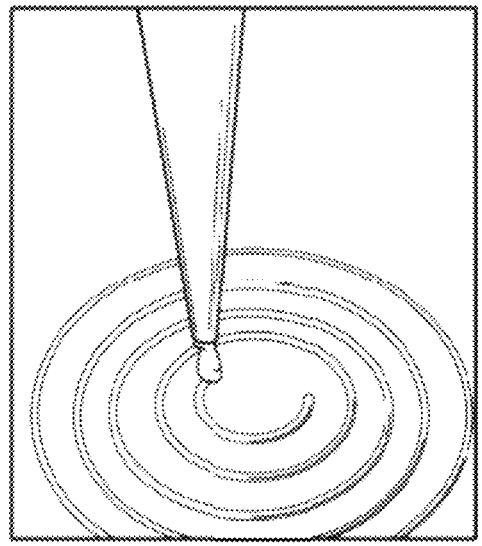
FIGS. 8A, 8B, and 8C are schematic representations that show an example of a tympanic membrane graft scaffold being printed by a 3D printer.
Figure 8B:
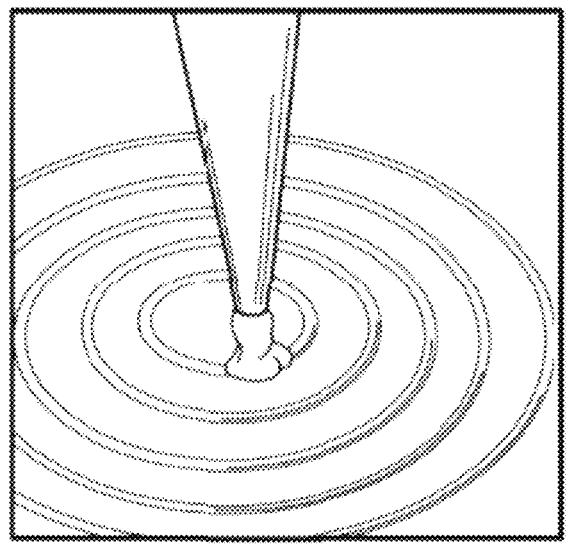
Figure 8C:
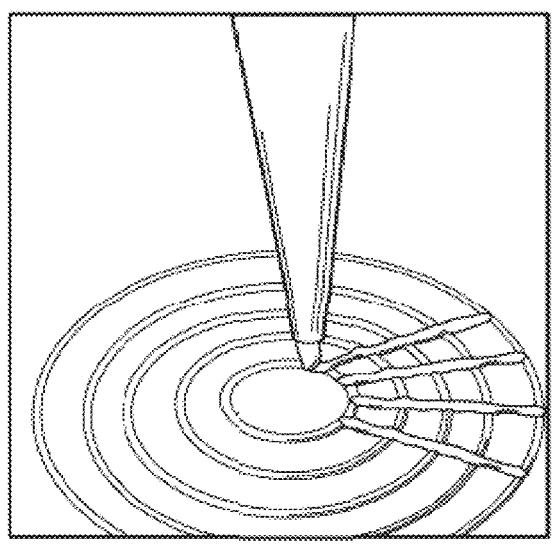

The printer 504 can print 518 the scaffold. FIGS. 8A, 8B, and 8C show an example of a tympanic membrane graft or bilayer graft scaffold being printed by a 3D printer. For example, the printer 504 generates a print job from the build plans and begin printing the scaffold. In general, most printers 504 include a mechanism for creating a solid object from gel, liquid or powder. In one example, a printer 504 can include a nozzle for extruding build material onto a substrate. The printer 504 controls the location of the nozzle in two dimension (e.g., x and y), and may control the elevation of the substrate in the third dimension (e.g., z). In some cases, the scaffold may be printed in a single layer, in which case the elevation of the substrate may be held constant during the printing process. In some cases, the scaffold may be printed in multiple layers or printed on an uneven surface (e.g., cone) to obtain a thin 3-dimensional shape, in which case the elevation of the substrate may be moved, e.g., lowered, from one layer to the next.

The nozzle of the printer 504 can be made of, for example, glass or a metal such as aluminum or stainless steel. The build material can be extruded through the opening of the nozzle, and may then form a layer of thickness based on the size of the nozzle opening. Some example nozzles may have an opening on the order of microns in diameter. For example, the nozzle opening may be 2, 5, 10, 25, 75, 100, 120, 150, 175, 200, 225, 250, 275, 300, 333, 475, 500, or 520 microns, a value in between, or more or less as is technologically appropriate.

The substrate that receives the printed scaffold can be made of a material appropriate for the build material. For example, the substrate material can be selected based on the materials cohesion properties with the build material so that the scaffold does not move as it is being printed, but can reliably be removed when the printing process is completed. Examples of substrate materials include, but are not limited to, glass (e.g., pluronic-coated glass), poloxamer, polytetrafluoroethylene (PTFE), metal foil such as aluminum foil, or biodegradable material, such as cellulose, for example. The substrate can be either flat or 3-dimensional in shape, allowing a thin construct to be created with depth (e.g. a conical membrane). The scaffold is then deposited onto the substrate, e.g., as a series of circular rib structures (as shown in FIGS. 8A and 8C) and/or radial rib structures (as shown in FIG. 8C).

The scaffold can be cured (step 520). For example, the material handling system may move the scaffold to the curing oven and plasma treater 506, and send a command signal to the curing oven. The curing oven may then cure the scaffold for a time and at a temperature indicated by the build plans 516.

The scaffold can be plasma treated (step 522). For example, the curing oven and plasma treater 506 can apply a plasma treatment specified by the build plan 516. This plasma treatment may, for example clean the scaffold and/or alter the surface properties of the scaffold After receiving the build plans, the hot plate and infill station 508 prepares the identified infill material. For example, the hot plate and infill station 508 may perform this operation while the scaffold is being printed, in response to an indication that the scaffold has been printed, or at a particular time.

The hot plate and infill station 508 can receive the infill material or materials in liquid form, for example from an automated or human operated source. If needed, the well station can also prepare any environmental conditions necessary for the infilling as specified in the build plan or otherwise. For example, a fan in a vent hood may be activated, air temperature or humidity may be controlled, and/or illumination may be increased or reduced.

If needed, other materials can be added. For example, any drug, growth factors, and/or cellular adhesion and invasion material can be added. The order of addition and type of mixing, if any, is specified based on the types of materials. For example, a non-volatile liquid may be added first, followed by a volatile liquid so that the volatile liquid has less time to evaporate. In another example, two or more materials may be mixed simultaneously.

Figure 8D:
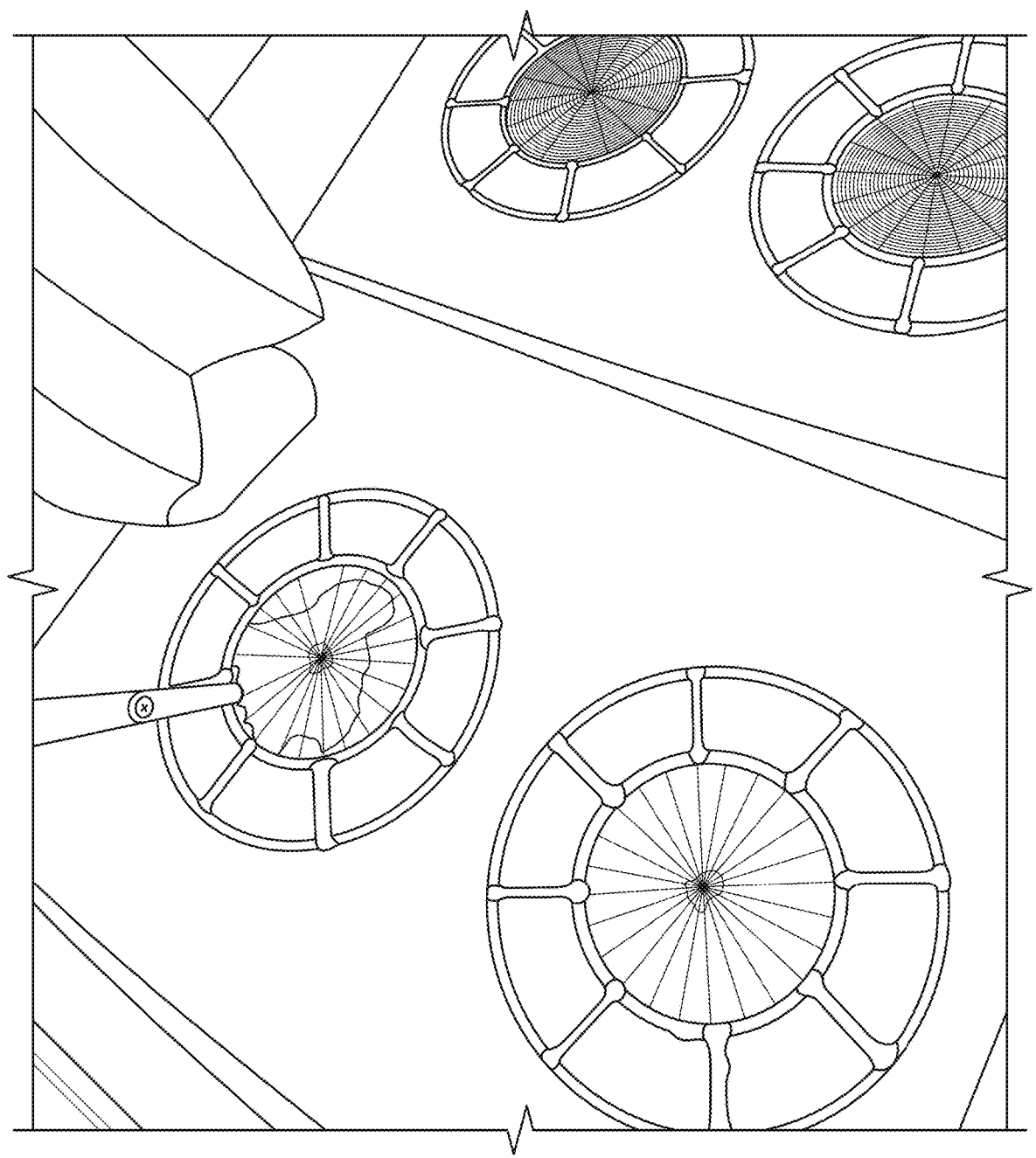
FIG. 8D shows the scaffold being filled with infill material.

The infill material is introduced to the scaffold 526. FIG. 8D shows an example of a tympanic membrane graft scaffold receiving infill material. For example, an automated material handler, e.g., an automated robot, or a human operator, can remove the scaffold from the curing oven and plasma treater 506 and add the scaffold to the hot plate and infill station 508. Here, the scaffold voids can be filled by the infill material. In some cases, the infill material may be pipetted into the voids of the scaffold, such as by a human or automated system. In some cases, submerging the scaffold in the infill material causes the voids to be infilled. In some cases, the container holding the scaffold and infill is agitated and/or the infill material is stirred to encourage the infill material to fill the voids. In some operations to fill the voids with the infill material, the scaffold may be flipped, and infill material is added to both sides of the scaffold. In some operations, flipping is not needed.

Figure 8E:
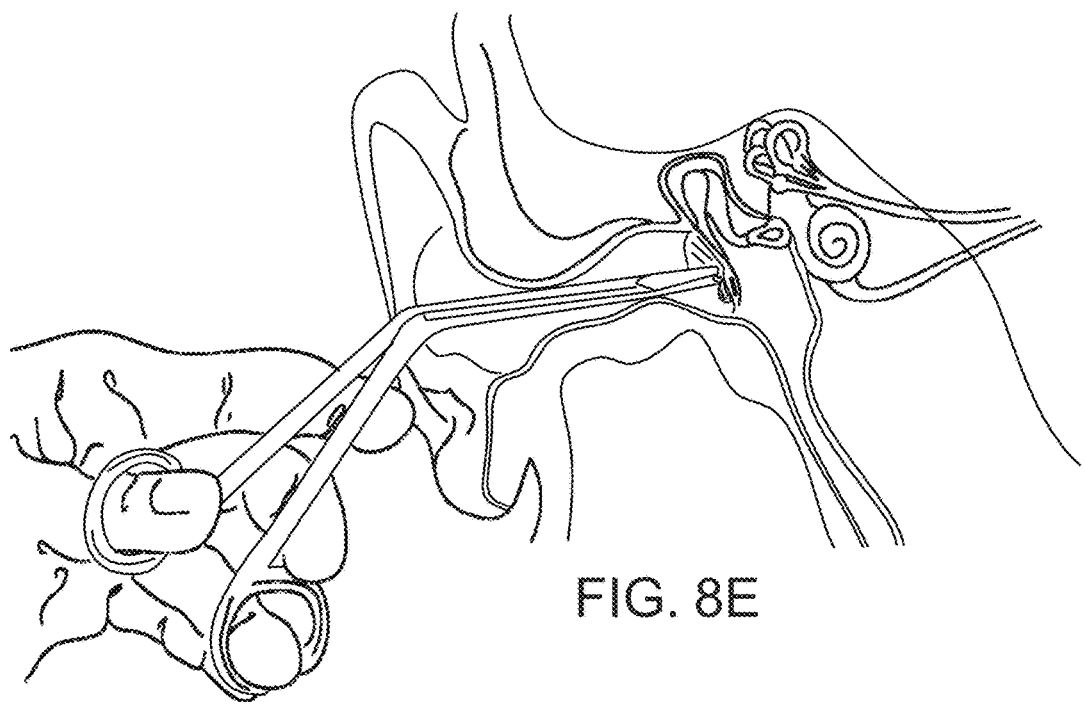
FIG. 8E is a schematic illustration of how a doctor can place one of the tympanic membrane graft devices into the ear canal and onto the tympanic membrane.

After the infill material fills the voids of the scaffold, the material handling system can move the uncured tympanic membrane graft to the incubator 510. The incubator can incubate and store 526 the tympanic membrane graft so that the tympanic membrane graft is a single, solid article. The configuration of the incubator 510 is designed based on the infill material and/or other materials. For example, the incubator 510 may include a temperature controlled waterbath, a humidity controlled air-hood, or any other technologically appropriate system for curing the infill material. Once the device is completed, it can be implanted onto or into a tympanic membrane (or replace a tympanic membrane), as shown schematically in FIG. 8E, in order to perform a tympanoplasty underlay and overlay. This represents the methods by which ear drum repair can occur without need for general anesthesia or sedation. Of course, in certain situations, sedation or anesthesia may be required.

Graft Properties

As described previously, the tympanic graft's geometric properties are specified in advance, e.g., based on the specific patient or group of patients who is or are to receive the graft. These properties may be determined in general (a particular size and shape for humans or other subjects, e.g., a different size and shape for guinea pigs, lambs, chinchillas, sheep, dogs, cats, horses, monkeys, etc.), or in the specific (based on measurements or imaging of a particular patient).

A tympanic membrane graft is generally designed to be acoustically tuned, resistant to perforation and retraction, and/or to provide a robust attachment point to the ossicular chain, such as direct connection to the malleus, incus, stapes, remnant of one of these ossicles, to a commercially available prosthesis, or in the case of disease, or completely replace the ossicular chain and connect directly to the oval window of the cochlea. For example, the tympanic membrane graft may be made of materials that have greater mechanical strength than a naturally occurring tympanic membrane or membrane graft, which reduces the chance of perforations and/or retraction. In other embodiments, the material may be stable in size and flexibility, which can help avoid retraction and provide for secure attachment to any component of the ossicular chain or directly to the oval window.

By selection of scaffold material and/or infill material, a tympanic membrane graft may be made to be impermeable to keep air, fluids such as water, and debris from entering the middle ear. On the other hand, the tympanic membrane graft may be made of a material that is permeable to air, but to keep liquids out. This may allow, for example, air pressure in the middle ear to normalize with the pressure in the outer ear. This may be desirable for patients with poor ventilation through the Eustachian tube. Additionally, the tympanic membrane graft may be made of material that is also permeable to small molecules and/or biologics, termed "semipermeable membrane." A semipermeable membrane may allow for the transmission of, for example, steroids, antibiotics, inflammatory mediators, and or other medications through the tympanic membrane graft allowing drug delivery to the middle ear and/or inner ear.

Graft Uses and Methods of Implanting

The artificial tympanic membrane grafts described herein can be used for any appropriate tympanoplasty and/or myringoplasty operations for the reconstruction of a patient's tympanic membrane, including for use in both human and non-human patients. The bilayer graft devices can be used to simply and effectively seal tympanic membrane perforations as a minimally invasive method of tympanic membrane repair.

In many procedures, access to the tympanic membrane may be through the ear canal itself, serving as a surgical portal, or an incision is made behind or in front of the ear to access the tympanic membrane in need of the graft. These incisions may be one of an endaural incision or a postauricular incision. Once access to the patient's tympanic membrane is achieved, the native (diseased or remnant) tympanic membrane may be removed and reconstructed in entirety (total tympanic membrane replacement) or in parts (patch/partial), or laid on top of an existing tympanic membrane with a defect (lateral myringoplasty), as a patch.

Once the artificial membrane graft is in place, the manubrium of the malleus (if present) is ensured to be contacting the surface of the membrane, drawing the membrane toward the tympanic cavity. Materials may be used to ensure adhesion and attachment of the manubrium to the artificial membrane. Attachment of the artificial membrane to the ossicles may cause the lateral surface of the membrane to become concave and conical in shape. The depth of conical shape can be assed prior to graft placement and selected appropriately. The malleus can then be attached to the lowest or most depressed part of the concavity of the membrane (e.g., at the location of an artificial umbo serving as an ossicular connector.)

There are variants possible, depending on the particular needs of a patient. For example, a tympanic membrane graft without an ossicular connector can be placed over native ossicular chain, healing directly to the manubrium of the malleus. A tympanic membrane with ossicular connector that attaches to the malleus may be used if the malleus was diseased or partially foreshortened. The graft could connect to the remnant malleus via a socket for the remnant bone. This socket could be made by preoperative imaging, or be created to a standard geometry.

A tympanic membrane with an ossicular connector that connects to the incus or remnant incus can also be used. In one configuration, a ring is incorporated into the tympanic membrane to allow a prosthetic to be attached to the ring and extend down to the incus. This connector would allow stable reconstruction of hearing. In other embodiments, a tympanic membrane with an ossicular connector that connects to the stapes or a stapes remnant can be used. This embodiment also takes the form a ring attached to the undersurface of the graft and would allow a prosthetic to sit atop the stapes with a wire that hooks through the ring. The connector can be made of nitinol, which allows a laser to be used to activate the "metal memory" and tighten the prosthesis down to the surrounding structures and over the ring. Other configurations of the ossicular connector are also possible and would include a ring, hinge, ball and socket joint or sliding joint.

Figure 9A:
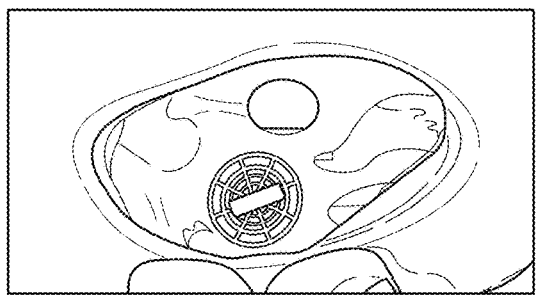
FIGS. 9A-9D are schematic representations of the use of the bilayer graft devices described herein to seal a tympanic membrane perforation.
Figure 9B:
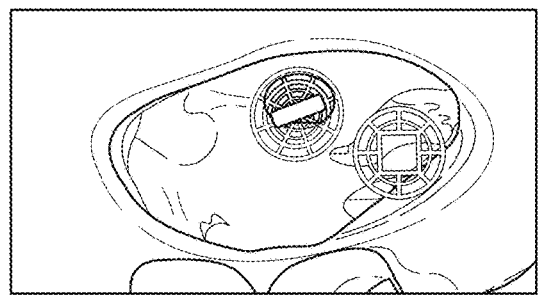

The new bilayer graft devices are installed to repair a tympanic membrane perforation in a multistep process as shown in FIGS. 9A to 9D. First, as shown in FIG. 9A, the perforation in the tympanic membrane is analyzed to determine the size and shape. Next, as shown in FIG. 9B, the underlay graft device is curled or rolled to reduce the overall size so that it can be pushed through the perforation and unfurled once behind the tympanic membrane so that the projection protrudes through the perforation. The top surface of the underlay device will adhere to the back surface of the tympanic membrane by capillary action or adhesion, or a tissue adhesive, such as a fibrin glue can be applied to the surface of the underlay device, e.g., just prior to insertion.

Figure 9C:
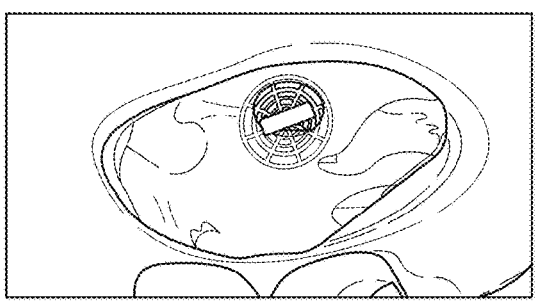
Figure 9D:
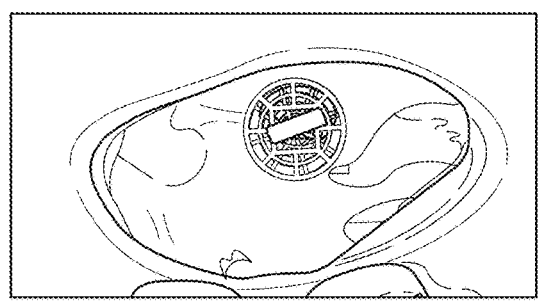

Next, as shown in FIG. 9C, the overlay graft device is brought into proximity of the underlay device. Next, the projection is pulled through the perforation and the opening in the overlay device. As shown in FIG. 9D, the overlay device is then rotated about a central axis so that the top of the projection, which generally does not move (or is held in place so as not to move), is securely fit onto the surface of the overlay device to lock the underlay and overlay devices together, sandwiching the tympanic membrane between them. FIG. 9D shows how the rectangular projection is offset at a slight angle with respect to the opening in the overlay device.

Figure 10A:
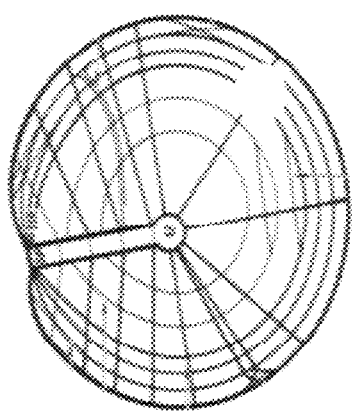
FIGS. 10A-10D are a series of schematic diagrams showing a fiber/rib arrangement template (FIG. 10A), a tympanic membrane perforation imaged onto the fiber template (FIG. 10B), a customized tympanic membrane patch graft or bilayer graft device in which the central region includes ribs designed to match the ribs in the location of the perforation (FIG. 10C), and placement of the device over the perforation to effect repair (FIG. 10D).
Figure 10B:
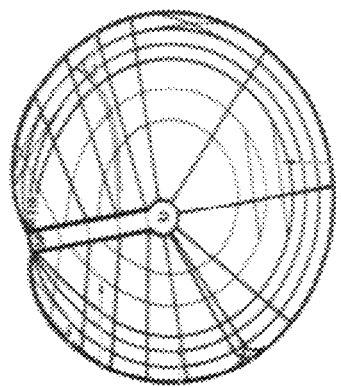
Figure 10C:
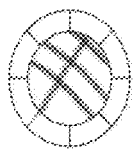
Figure 10D:
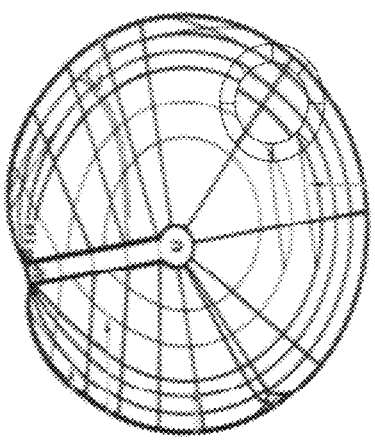

FIGS. 10A-10D show another repair in which the ribs of the graft device are designed to match the structure of the tympanic membrane to be repaired. In particular, FIGS. 10A-10D show a fiber/rib arrangement template based on images of the tympanic membrane to be repaired (FIG. 10A), a tympanic membrane perforation imaged onto the fiber template (FIG. 10B), a customized tympanic membrane patch graft or bilayer graft device in which the central region includes ribs designed to match the natural structure in the location of the perforation (FIG. 10C), and placement of the device over the perforation to effect repair (FIG. 10D).

Alternatives

While various arrangements of scaffolds and voids are described and shown herein, other arrangements are possible. Other examples of arrangements can include ribs formed in true circle shapes, or irregular circular shapes. In some other examples, the ribs of a scaffold may conform to a different configuration. For example, a scaffold may be formed of generally straight ribs, some of which are offset by an angle (e.g., 45° or 90°) to form a regular pattern or mesh, e.g., of triangular, square, parallelogram, hexagonal (see, e.g., FIGS. 3C-A and 3C-B), or other shapes. In another example, the shape of each rib may be created to reflect natural patterns, e.g., Brownian motion or fractal patterns, to form an irregular mesh, or random patterns can be created.

As noted above, drugs, growth factors, and/or cellular adhesion and invasion materials can be mixed with or added to the infill material or scaffold material or coated onto or soaked into the scaffold and/or infill material. However, in some implementations, some or all of these drugs, growth factors, and/or cellular adhesion and invasion materials can instead be applied to the exterior surfaces of the graft devices either before or after implantation. This may be desirable, for example, when using a mass produced graft without such an application, but where a drug, growth factor, and/or cellular adhesion and invasion material is added for a particular patient.

As described above, different processes of manufacture can be used to create the graft devices described herein. For example, instead of filling the voids of the scaffold by submerging the scaffold in the infill fluid, the voids may be filled by 3D printing. For example, some 3D printers allow for multiple print materials to be used in a single device. In such a printer, the scaffold could be printed with a first material, and a second material could be printed into the voids. Alternatively, the finished scaffold could be loaded into a different 3D printer that is instructed to print the infill material into the finished scaffold's voids.

In some cases, the infill material may be the same material as used to form the scaffold. For example, after printing the scaffold, the same 3D printer may print the infill material in the voids. By doing so, the mechanical properties of the scaffold may be preserved, even as the entire graft is printed of a single material.

EXAMPLES

The invention is further described in the following examples, which do not limit the scope of the invention described in the claims.

Example 1—Printing a Scaffold

This example covers the creation of a tympanic membrane graft scaffold designed based on a human tympanic membrane.

The ultrastructure of the human tympanic membrane was analyzed and a computerized 3D model of the membrane's fibrous layer was created. Rib pattern, thickness, and 3D conical configurations served as design variables for the printed scaffold.

A multilayered, artificial tympanic membrane graft scaffold was fabricated using a 3D printer. The scaffold was printed with polydimethylsiloxane (PDMS) ink in a pattern derived from the examination of the human tympanic membrane, with a rib thickness of 120 microns, an overall diameter of 12 millimeters, and a 3D conical configuration. The scaffold, when printing was complete, was heat cured and removed from the substrate using forceps. Examples of printed tympanic membrane graft scaffolds are shown in FIGS. 2A to 2E.

FIG. 2A shows a top view of a graft device scaffold, with the central regions filled with an infill material. FIG. 2B shows a graft device with a single ring design for attachment to the ossicular chain. FIG. 2C shows a graft device with a single arch ring design for attachment to the ossicular chain. FIG. 2D shows a graft device with a double arch ring design for attachment to the ossicular chain.

FIGS. 2E-A to 2E-D are photographic representations of tympanic membrane patch graft scaffolds that were designed and printed at a total diameter of 5 mm in two fiber configurations: 4 radial (R) and 4 arc (A) fibers and 6R and 6A fibers. Radial and circumferential fiber configurations were chosen based on the desire to mimic the basic circumferential and radial fiber arrangement of the human tympanic membrane, to achieve consistency among printing results, and to obtain the ability to easily manipulate fiber arrangement. Using the same material, a thicker peripheral border region was also printed to stabilize the TM patch scaffold and allow appropriate positioning for cell studies. The border region consisted of one outer ring intersecting the outmost vertices of the inner square tympanic membrane graft patch scaffold, with linear fibers connecting the midpoint of each side of the scaffold to the border ring.

These results demonstrate that a tympanic membrane graft can be fabricated based on a 3D printed scaffold having voids to be filled with an infilled material.

Example 2—Infilling Voids of a Scaffold

This example covers the infilling of a tympanic membrane graft scaffold with an infill material to create a solid graft. An infill mixture of type III collagen with fibrin 30% was prepared and placed into a pipette. A printed tympanic membrane graft scaffold was placed into a circular well using forceps, as shown in FIG. 5A. Next, the infill material was introduced into the voids of the scaffold, as shown in FIG. 8D. The scaffold was allowed to rest in the collagen for twenty minutes at 37° Celsius. Using forceps, the graft was removed from the well and placed in deionized water in a 37° Celsius incubator. FIG. 5B shows the graft with the collagen filling the voids of the scaffold. These results demonstrate that an infill material can be used to fill the voids of a scaffold and cured to create a tympanic membrane graft.

Example 3—In Vitro Cell Studies

This example covers experiments designed to determine if human neonatal dermal fibroblasts will colonize and grow over non-absorbable (PDMS) or absorbable (PLA) tympanic membrane grafts in vitro.

Figures 1, 11A:
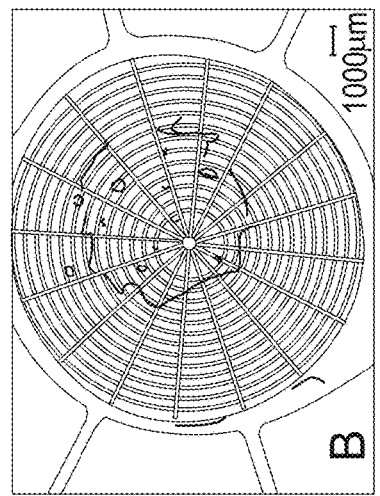
FIGS. 11A-1 to 11A-4 are photographic representations of a PDMS scaffold (11A-1), a collagen/fibrin infilled scaffold (11A-2), a magnified image of FIG. 11A-2, showing cells growing on the device (11A-3), and a further magnification of FIG. 11A-3 (11A-4).
Figures 2, 11A:
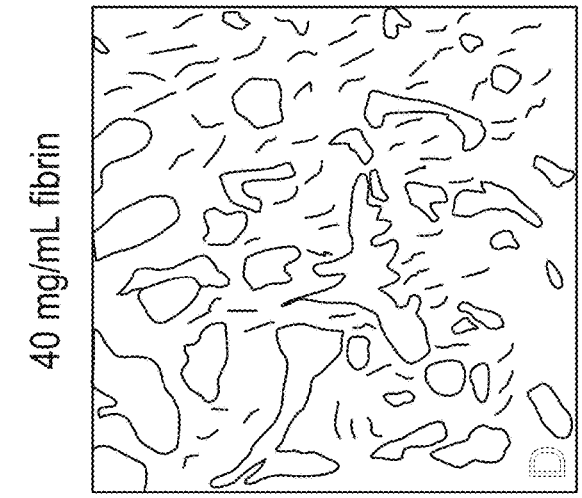

PDMS or PLA scaffolds were prepared as described in Example 1, and as shown in FIG. 11A-1. Some were then coated with a fibrin/collagen infill mixture as described in Example 2, and the results are shown in FIG. 11A-2. Scaffolds and infill, once cured and solidified, were then placed in cell culture dishes with neonatal dermal fibroblasts. GFP (green fluorescent protein) expressing human neonatal dermal fibroblasts (HNDFs) were seeded at 200,000 cells/well into 6-well plates and allowed twenty four hours to adhere to the dish to form confluent layers. During this time, the tympanic membrane grafts were submerged in media overnight in an incubator. The tympanic membrane grafts were laid directly on top of the confluent layer of HNDFs and held down with glass slide pieces to have contact with the HNDFs and to inhibit floating. The glass pieces were removed after twenty four hours and imaging was conducted after six days (144 hours).

Figures 3, 11A:
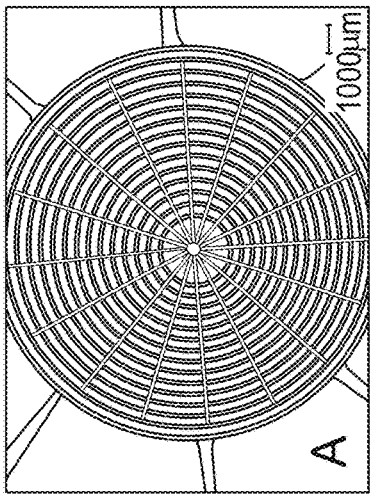
Figures 4, 11A:
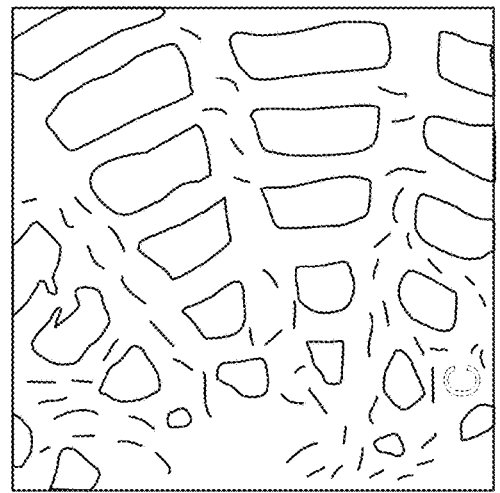
Figures 1, 2, 11B:
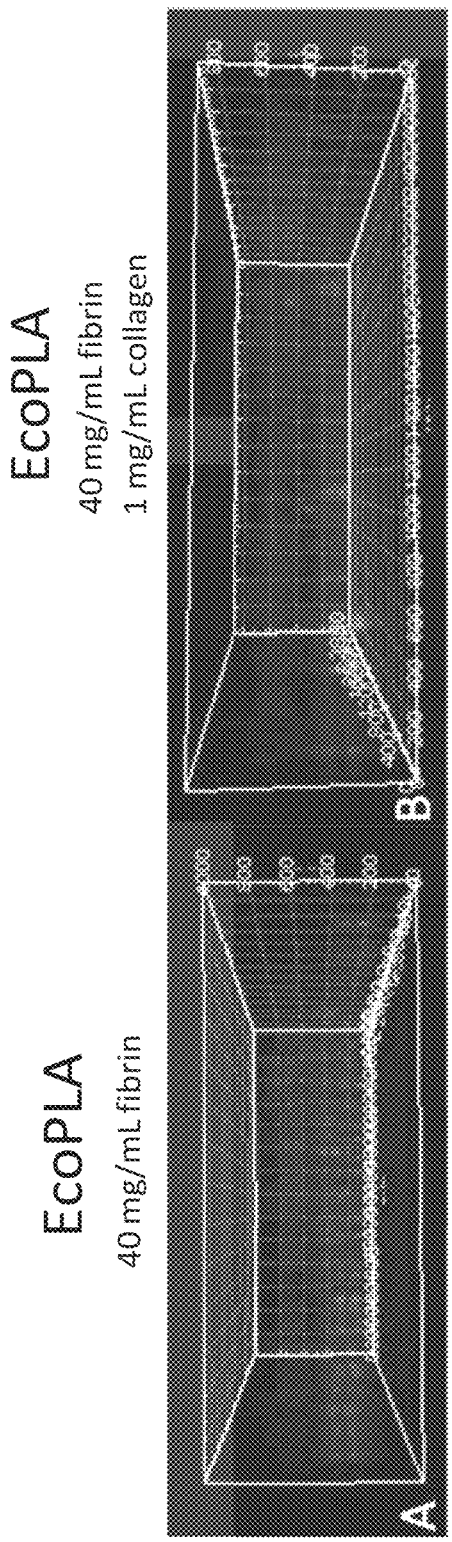

FIGS. 11A-3 and 11A-4 show height maps showing the location of HNDFs in the z-axis following 6 days adjacent to 200,000 HNDFs per well. Red (gray) represents HNDFs on the bottom of the well plate and green (light gray) represents HNDFs at the top of the viewing plane. FIGS. 11B-1 and 11B-2 are confocal microscope z-stack images that demonstrate cellular growth over PLA scaffolds with either fibrin infill alone or fibrin/collagen infill. FIGS. 11B-1 and 11B-2 present the same data that is shown in FIG. 11A-4 from a different view, along the Y axis while FIG. 11A-4 is shown along the Z axis.

These studies demonstrate that cells were able to grow on the surfaces scaffolds and infill materials. In addition, these studies demonstrate that the scaffold and infill materials (PDMS/PLA/Fibrin/Collagen) are not toxic to fibroblasts and would allow cellular ingrowth and adhesion following implantation. As a cellular toxicity study, we find these to be reasonable materials for use as tympanic membrane implants. Particularly, this type of cell growth shows that there will be cellular growth over and into the graft from the middle ear and external auditory canal, ensuring graft take.

Example 4—Acoustic and Mechanical Testing

Acoustic testing was designed to determine the acoustic properties of non-absorbable and absorbable grafts in relationship to temporalis fascia and normal tympanic membrane with an intact ossicular chain. The human tympanic membrane fibrous layer was examined using electron microscopy and used as the basis for initial tympanic membrane design. Biocompatible absorbable and non-absorbable materials were printed as thin sheets and patterned tympanic membrane scaffolds. Scaffolds were layered with fibrin/collagen infill to create an impermeable membrane as described in Examples 1 and 2 above. In particular, scaffolds of varying diameters (8-12 mm), thicknesses (50-200 microns), and radial rib arrangements (4-32 ribs) were successfully printed and layered with semi-translucent collagen/fibrin infill.

Acoustic properties of printed tympanic membranes were then determined by digital opto-electronic holography and compared to fresh human cadaveric temporalis fascia and human cadaveric tympanic membranes with intact ossicular chains. Printed and infilled tympanic membranes were mounted in artificial external auditory canal holders replicating the environment of the external auditory canal at 9 mm in diameter and 25 mm in length. Grafts can be coated with titanium dioxide to improve reflectance of the surface of the material. Mounted grafts were subjected to total sound pressures of brief duration (tone pips) at 5 different frequencies appreciated by humans and regularly tested during audiograms: from 0.5-15 kHz. Sound pressure amplitudes ranged from 80-110 dB SPL and pulse width of 50-100 µs. Sound stimuli are generated by broadband sound sources driven by a power amplifier through the long end of the artificial external auditory canals.

Digital Opto-Electronic Holography (DOEH) provides real-time-averaged holograms of membrane motion, providing qualitative and quantitative full-field information on the sound induced motion of TM grafts. FIGS. 12A-A to 12A-G show images of examples of different graft testing holders. FIGS. 12A-A to 12A-D are computer-generated images of a lid (A) and base (B) of one version of a graft holder that uses a piston design to keep the tympanic membrane graft in place. The holder included a well for secure placement of a single TM composite graft or temporalis fascia. The cap was designed to completely cover the border region such that only the scaffold and collagen/fibrin infill were subject to acoustic testing. Examples of dimensions for the base can be: inner hole diameter of 9 mm, well diameter of 25.5 mm, outer diameter of 35 mm, inner well depth of 3 mm, and total length of 30 mm. The cap can have the same inner and outer radii as the base with an extruded portion diameter of 25 mm, extruded portion length of 2.5 mm, and total length of 5.5 mm. Images in FIGS. 12A-C and 12A-D show the lid and holder of another version of the tympanic membrane graft holder that uses a sliding mechanism to secure the tympanic membrane graft for testing. FIG. 12A-E is a photo that shows actual fabrications of the computer images of FIGS. 12A-A to 12A-D. FIG. 12A-F shows a 3D printed tympanic membrane graft inside of the testing device shown in FIGS. 12A-C/D. FIG. 12A-G shows the graft holder when closed. These holders are used in a holography and mechanical impedance testing system.

Figure 12A:
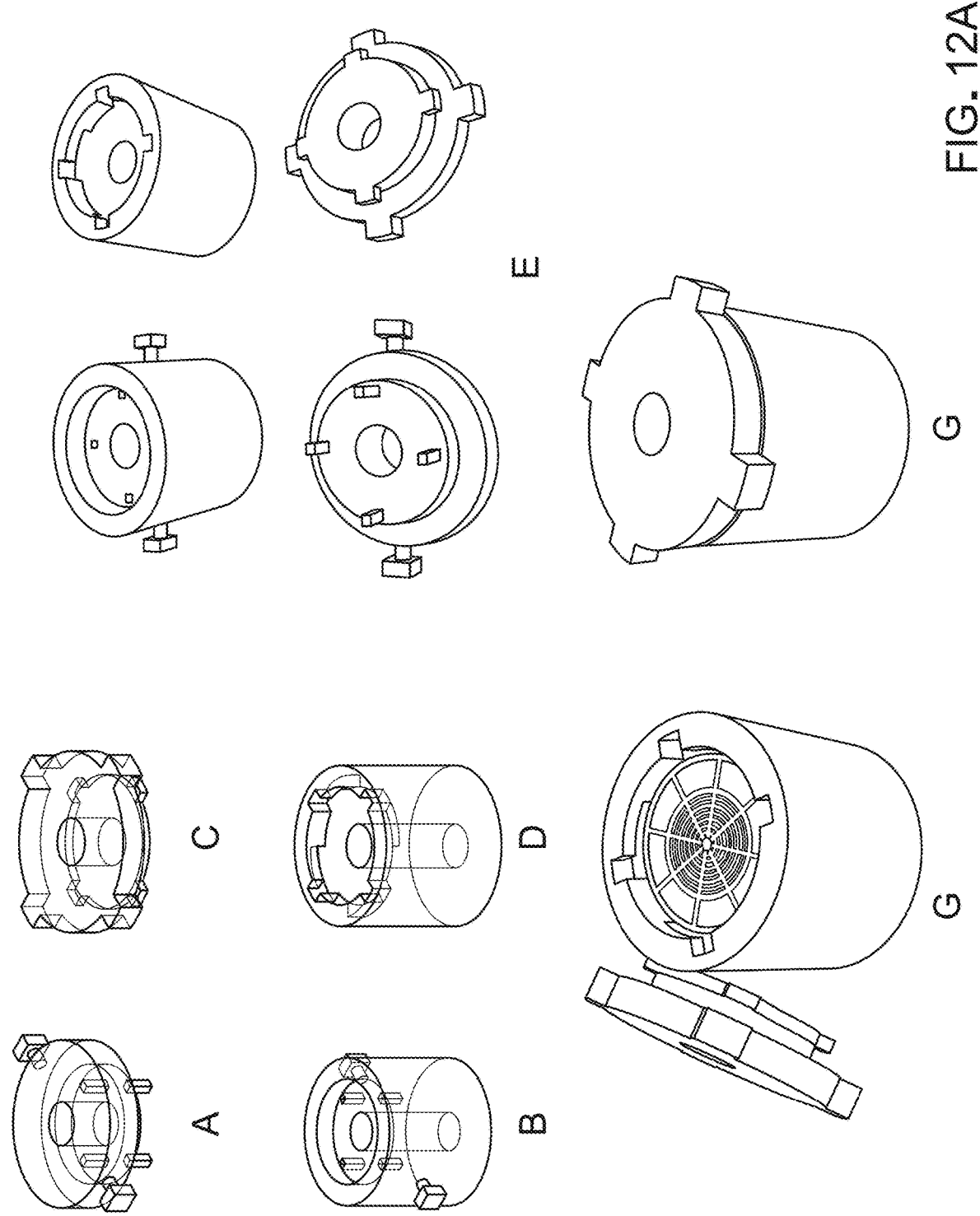
Figure 12B:
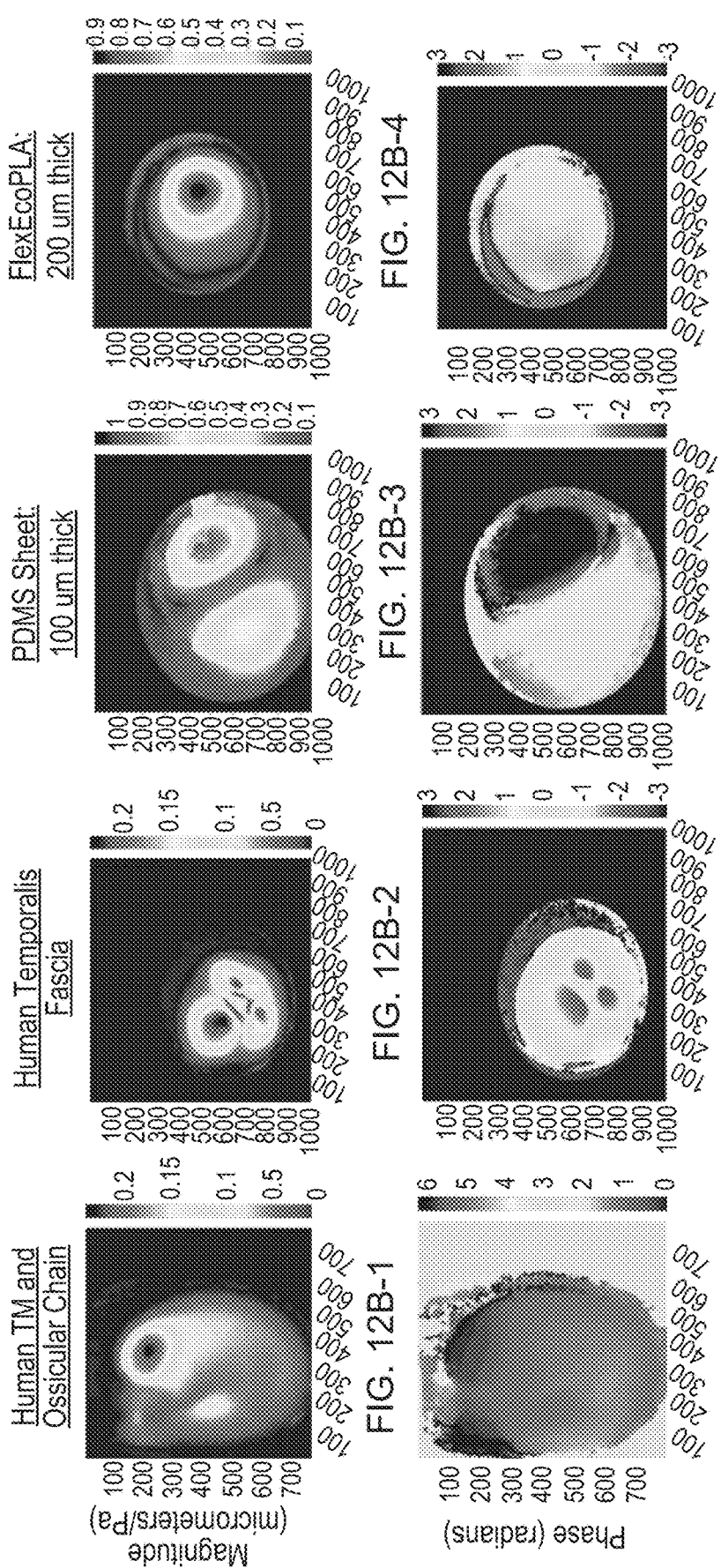

Mounted grafts were subjected to DOEH to assess magnitude and phase angle of motion following acoustic stimulation. Both modal responses to uniform stimulation, as well as traveling wave-dominated motions of the 3D printed tympanic membrane were recorded. To determine the appropriate thickness of a 3D printed tympanic graft, preliminary experiments were conducted to understand how materials and thicknesses affect displacement in response to acoustic energy. A host of materials and thicknesses were tested and representative images are shown. FIGS. 12B-1 to 12B-4 demonstrate similar displacement magnitudes of 3D printed sheets of PDMS or PLA compared to human tympanic membrane attached to ossicular chain and human temporalis fascia, which is a currently used tympanic membrane graft material during tympanoplasty. FIG. 12B-1 demonstrates normal displacement magnitude of tympanic membrane attached to an ossicular chain in a human cadaveric temporal bone. Maximum displacement of human TM in temporal bone model was around 0.25 micrometers.

Three comparison groups are shown: human temporalis fascia shown in FIG. 12B-2, PDMS (100 microns thick) shown in FIG. 12B-3, and FlexEco™ PLA (200 microns thick) shown in FIG. 12B-4. These comparison data demonstrate similar displacement magnitudes. Slight increases in displacement of human temporalis fascia, PDMS, and PLA as compared to human cadaveric tympanic membrane in a temporal bone may be due to an absence of a dampening effect from the lack of an intact ossicular chain in the models. The bottom row of figures (FIGS. 12B-5 to 12B-8) demonstrate the different phase of the tympanic membrane in response to sound. FIG. 12B-5 demonstrates a uniform pattern of tympanic membrane which is connected to the ossicular chain. FIGS. 12B-6 to 12B-8 demonstrate that FlexEco PLA (12B-8) and PDMS devices (12B-7) both show similar phase distributions compared to human TM (12B-5), but vary slightly compared to devices made of temporalis fascia (12B-6).

Figure 12C:
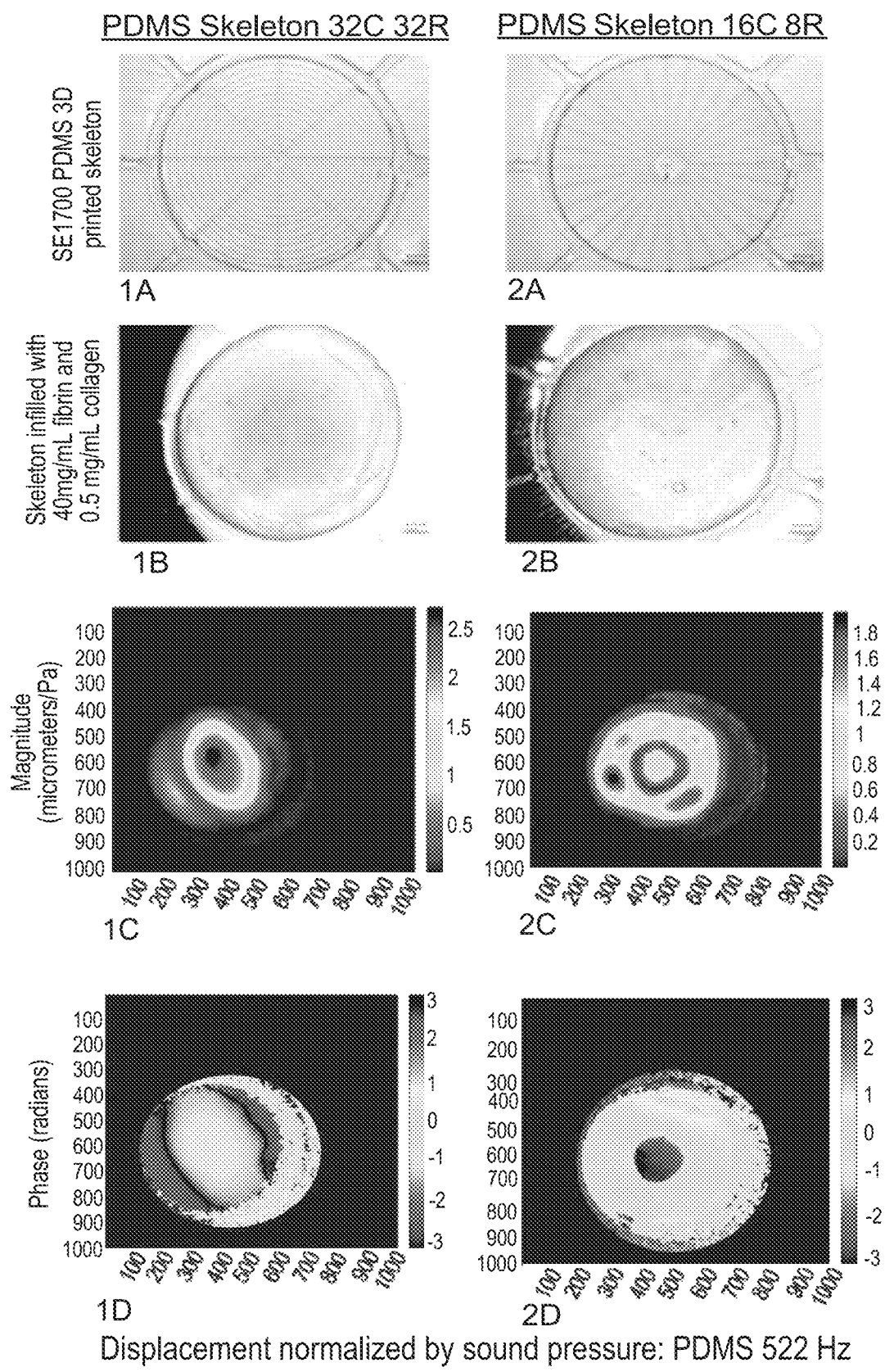

A representative comparison of acoustic properties of 3D printed tympanic membrane graft influenced by fiber arrangement was performed using digital opto-electronic holography after response to a 522 Hz pure tone sound. FIG. 12C, the top row shows the 3D printed rib structure of SE1700 PDMS in two configurations, one with 32 circular (C) ribs and 32 radial ribs (R) (FIG. 12C-1A) and one with 16C ribs and 8R ribs (FIG. 12C-2A) on a BYTAC Teflon™ printing surface. The second row shows these same scaffolds infilled with a collagen/fibrin mixture (FIGS. 12C-1B and 12C-2B). The third row demonstrates magnitude of displacement of these same PDMS scaffolds (FIGS. 12C-1C and 12C-2C). Note similar displacement magnitudes demonstrating that rib motion, differs based on scaffold rib arrangement. FIGS. 12C-1D and 12C-2D show clear differences in phases based on rib count and arrangement. This implies a "tunability" of TM grafts based on rib count and arrangement.

A representative comparison of human TM and attached ossicular chain to 3D printed tympanic membrane graft with 32 circular ribs and 32 radial ribs to high frequency pure tone sound was performed. FIGS. 12D-1A and 12D-2A show the magnitude of displacement of a human TM and ossicular chain compared to a PDMS scaffold with 32 circular scaffold ribs and 32 radial ribs, respectively (note similarities in magnitude of displacement, as well as complex waves). FIGS. 12D-1B and 12D-2B show the complicated phase patterns of both human TM with ossicular chain as well as a 3D printed tympanic membrane, respectively.

Digital Opto-Electronic Holography results were compared to acquired data on the native human tympanic membrane. Within 3D printed materials, a relationship between specific acoustic properties (magnitude and phase angle) and structure (rib size and orientation) was determined. Optimal acoustic properties were defined as those of a normal healthy human tympanic membrane.

Printed sheets and scaffolds with infill showed frequency dependent variations in motion patterns (number and location of peaks) at 1000, 4000, and 8000 Hz. The motion patterns were affected by the materials used to prepare the sheets and also were affected by the rib patterns of the scaffolds. Certain materials and designs of tympanic membrane scaffolds showed similar motion patterns to human tympanic membrane and fascia. The normalized displacement magnitude (micrometers/Pa) of sheets and scaffold and infill were similar to displacement of fascia and tympanic membranes.

Additional testing for the 3D printing tympanic membrane grafts includes mechanical testing, which included determination of distensibility to negative and positive pressures. The pressure of the middle ear ranges from +50 to −200 d Pa. In chronic Eustachian tube dysfunction (ETD), there may be continued negative pressure in the middle ear. Using a tympanic membrane holder in a sealed vacuum chamber, the 3D tympanic membrane graft is exposed to negative or positive pressure at a variety of physiologic and/or supra-physiologic values for several time points, such as one day, one week, and one month. The tympanic membrane grafts are then examined by microscopy to determine any change in overall shape and ultrastructure. Human temporalis fascia undergoes similar testing and serves as a control. Additional acoustic experiments include acoustic testing after negative or positive pressure and mechanical deformation to determine if there are any changes to acoustic properties and ultrastructure.

Additional testing for the 3D printing tympanic membrane graft included laser Doppler vibrometry ("LDV") measurements for tympanic membrane grafts of various materials. FIGS. 15A-D show velocity normalized by stimulus sound pressure of tympanic membrane composite grafts, fascia, and the human TM across the human frequency range. FIG. 15A shows the graphical results of comparison testing of all tested materials in which measured mean velocity for three specimens of 8C/8R TM composite grafts of varying composition (PDMS, PLA, and PCL), fascia, and human TMs with intact middle ears. FIGS. 15B-D show the graphical results for comparisons of grafts of different materials (PDMS, PLA, and PCL, respectively) with different designs (8C/8R and 16C/16R). Grafts of higher fiber count showed slightly lower mean velocities.

The results of these acoustic tests indicated that the materials and printing dimensions are useful as artificial tympanic membrane scaffolds and indicate they can be acoustically tuned. In addition, these tests confirm that the tympanic membrane graft devices and the bilayer graft devices can be acoustically tuned by, for example, changing the radial and circular rib arrangement, other geometric parameters, materials, etc. Sound-induced motion patterns of grafts that mirror the motion patterns of the tympanic membrane were determined and analyzed to alter the number of fibers/ribs and material type.

Example 5—Animal Studies—Guinea Pigs, Sheep, and Chinchillas

Guinea pig, sheep, and chinchilla models were used for ototoxicity and hearing tests. The guinea pig is a useful animal model for ototoxicity and hearing studies because the middle ear space is readily accessible and one can perform auditory brainstem responses (ABR) to determine hearing thresholds. Sheep are useful models for tympanic membrane graft studies. The chinchilla model is useful for ototoxicity testing and baseline ABR testing as well as distortion product otoacoustic emissions (DPOE) testing.

FIG. 13A shows a sheep model tympanic membrane with a perforation made. FIG. 13B shows a trimmed tympanic membrane graft in a sheep model. Size, accessibility, and the middle ear environment are generally reflective of the human ear. Sheep have been used for middle ear surgical training as well as for drug and device testing in otologic surgery. In addition, the tympanic membrane graft devices described herein are placed in cadaveric human tympanic membranes.

Ototoxicity studies were performed by using both physiology and histological experiments. For physiology experiments, animals undergo baseline auditory brainstem response (ABR) testing to determine baseline hearing threshold. Next a post-auricular incision is made, and the middle ear space is entered through the bulla. Following entry of the middle ear space, a host of different types of graft materials (as described above) are placed adjacent to the round window. The opening of the middle ear space is then covered with soft tissue, such as muscle and/or facia, the incision is sutured, and the animal allowed to recover. The animal then undergoes testing of hearing thresholds via ABR at 1 week, 2 weeks, 3 weeks, 1 month, 2 months, 3 months, up to 1 year or any permutation. Results suggest no ototoxic features of utilized materials (PDMS, PLA, PCL, collagen, fibrin, and hydrogel).

For histology experiments, the animals are perfused with saline and then paraformaldehyde. The middle ear and inner ear structures are then sectioned and histologically analyzed. Sections are reviewed for evidence of inflammation, calcium deposition, as well as markers of hair cell loss and neuronal loss in the cochlea. A variety of immunohistological stains are used for this purpose. In addition, the 3D printed material placed in the middle ear space is also examined by light, fluorescence, and/or electron microscopy to understand any signs of inflammation, degradation, or other changes.

For graft repair experiments in the sheep large animal model, animals are appropriately anesthetized. An incision is made in the tympanic membrane. The graft is then sized appropriately and placed over or under the defect, similar to human surgery.

The animals are allowed to recover. The contralateral ear or another animal with a similar defect made in the tympanic membrane but without the graft is used as a control. After every month up to 12 months, the animals are assessed for graft take, healing of the tympanic membrane and to determine any signs of infection, inflammation, shifting of graft materials or other notable changes. After similar time points, animals have the tympanic membrane graft with surrounding structures removed and analyzed histologically. The graft materials are examined by light, fluorescence, and/or electron microscopy to understand any signs of inflammation, degradation, or other changes.

FIGS. 14A to 14C show the use of a tympanic membrane graft "patch" as described herein to seal a perforation of a tympanic membrane in the chinchilla small animal model. The ototoxic potential of three specific 3D printed tympanic membrane composite grafts was tested by surgically implanting them within the chinchilla middle ear space. These graft devices were made of PDMS, PLA and PCL and 3D printed as described herein. The grafts scaffolds were then infilled with a bovine fibrin hydrogel. Anesthetized animals underwent baseline auditory brainstem response (ABR) and distortion product otoacoustic emissions (DPOE) measurements.

Under sterile conditions, the 3 mm TM grafts were placed through the bulla between the tympanic surface of the TM and the round window niche. As a control operation, the contralateral bulla was entered but no graft was placed. Physiologic responses to the surgery and graft implantation are assessed via ABR and DPOE at 3 or 6 months. The graft and inner ear of the chinchilla will be then be analyzed for inflammatory mediators using standard otopathology techniques and compared to the control ear. Immunohistochemical techniques will also be used to evaluate macrophage/monocyte markers such as IBA1, CD68, CD163, as well as CD45.

Chinchillas are a well-established inner and middle ear animal model and are commonly used for auditory research.

Based on preliminary animal tests, it appears that biomimetic grafts described herein, including the bilayer design, are not cochleotoxic. In cadaveric models they can be used to effectively repair a perforated tympanic membrane perforation.

Example 6—Tympanic Membrane Patch Graphs Having Conical Shapes

Figure 16A:
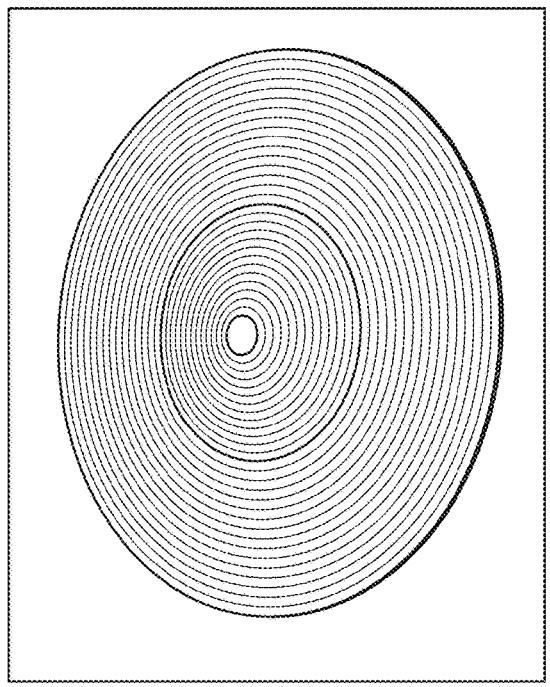
FIGS. 16A-C are photographic representations of tympanic membrane grafts having conical shapes.
Figure 16B:
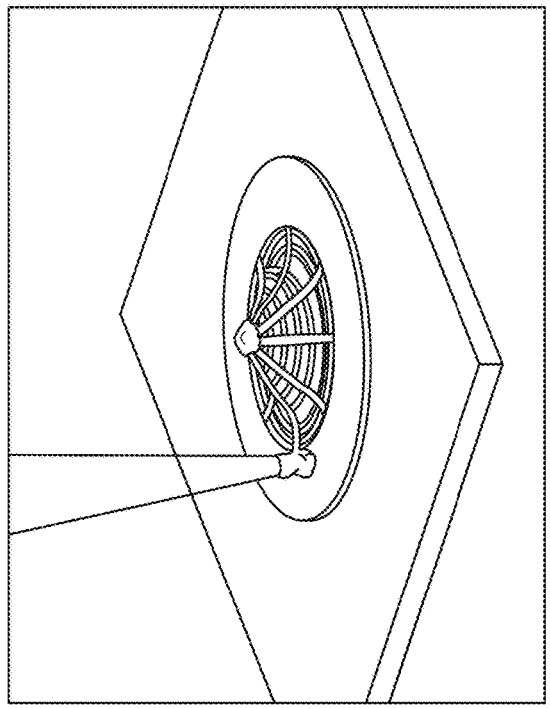
Figure 16C:
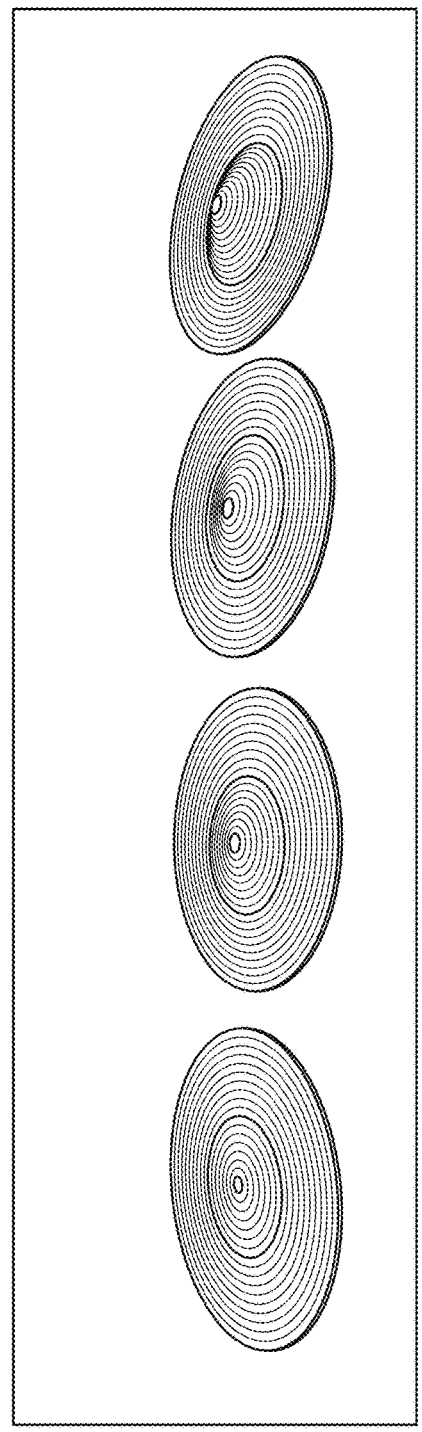

FIG. 16A-C are photographic representations of tympanic membrane patch graphs having conical shapes. FIG. 16A shows a conical shaped tympanic membrane graft with a central height of 2 mm. FIG. 16B shows a tympanic membrane graft scaffold of 8C/8R with a central height of 3 mm. FIG. 16C shows tympanic membrane grafts of varied heights.

Unlike fascia, which does not possess the fibrous scaffold architecture or conical shape of a human tympanic membrane, a 3D printed tympanic membrane graft may be created as described herein. Such a conical tympanic membrane graft may receive and transmit sound-induced motion patterns that are dependent upon the graft's conical depth.

Grafts were printed upon 3D molds of 9 mm diameter of varied conical heights (0 mm, 1 mm, 2 mm, and 3 mm). Direct ink writing was used to extrude PDMS through a 410 μm nozzles under ambient conditions in filamentary form to create solid sheets and scaffolds of 200 μm thickness. Tympanic membrane grafts of 8C/8R were infilled with an 80 mg/mL bovine fibrin hydrogel and stored in deionized water at 37° C.

To perform finite-element analysis (FEA), 3D geometry and mesh of 3D printed membranes were created. The geometries were discretized using 3D quadratic tetrahedral elements. Degrees of freedom were fixed where the membrane covered the holder surface in our experimental setup. Sinusoidal pressure was applied to the 9 mm membrane surface corresponding to the central cylindrical opening of the graft holder. The Young's modulus was considered to be 4.1 MPa and the damping ratio was considered to linearly increase from 0.056 at 200 Hz to 0.071 at 6300 Hz. Both material parameters were calculated based on laser Doppler vibrometry measurements using a mixed analytical-experimental method developed in our laboratory.

To perform digital opto-electronic holography (DOEH), an interferometer was used to record motion-induced holograms in real-time through two interfering laser beams, providing qualitative and quantitative full-field information of the sound induced motion of a membrane. The magnitude and phase angle of displacement of more than 400,000 points on the surface of a membrane were acquired simultaneously. A membrane was mounted in a holder with an integrated sound coupler, placed in front of the interferometer camera head, and oriented such that the surface of the membrane is perpendicular to the object beam of the laser. The membrane was held in the holder by a combination of viscous forces and negative pressure restricted to the membrane support. Pure tones (0.1, 1, 3 and 6 kHz) were played from the sound source and the displacement waveform for each point on the membrane surface is recorded in stroboscopic mode. Fourier transformations were used to compute displacement magnitude and phase at each point.

Cones of varying depth show frequency dependent surface motion patterns measured by DOEH. Surface motion patterns are progressive, from simple (<1000 Hz) to complex (3000 Hz), to highly ordered (6000 Hz). Absolute displacement magnitude value and patterns vary by cone height. Flat membranes tend to have larger motion than 1, 2, or 3 mm cones by a factor of 5-10 below 1000 Hz, while the differences become smaller at higher frequencies.

Finite element analysis (FEA) was predictive of surface motion patterns in response to sound. Differences in motion patterns and displacement amplitude by conical depth were predicted using FEA. Irregularities in printed grafts explain asymmetries in measured patterns. Nodes of maximal displacement appear asymmetrically in DOEH results and become more pronounced at greater conical depths. Irregularities in the manufacturing process of grafts leave a seam along solid membrane grafts, producing asymmetric motion. Infilled TM graft scaffolds demonstrate similar displacement to solid sheets. At low frequencies, surface motion patterns of PDMS 2 mm conical scaffolds, infilled with collagen/fibrin hydrogel, show simple, nodal patterns.

The results show that uncoupled human TMs have similar displacement patterns as the 3D graft devices described herein. The isolated TM (in annulus but without middle ear load) has measured displacement patterns that show some similarities to 2 mm solid cones and 2 mm in-filled graft scaffolds. However, in-filled grafts and conical membranes move somewhat less than the human TM.

Laser Doppler vibrometry ("LDV") results show that increasing conical depth results in higher stiffness at low frequencies. LDV measured velocity at the center point of printed grafts consistently demonstrates an inverse relationship between graft height and motion. This suggests that conical shape independently leads to increased stiffness of the membrane. Measured first resonant frequencies by flat and conical grafts demonstrate a progressive shift to higher frequencies for cones of greater depth. Velocity differences at high frequencies are less obvious. When comparing conical grafts of different heights, consistent differences are less apparent above 1000 Hz.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An artificial tympanic membrane device, comprising: a scaffold comprising a plurality of ribs comprising a first material or combination of materials, wherein the scaffold is approximately flat or has a shallow cone shape and a diameter of about 0.5 to about 19 millimeters, wherein at least one of the ribs of the scaffold forms a circular shape and two or more ribs of the scaffold form a radial pattern, and wherein the ribs have a diameter of about 5 to about 800 microns; and a plurality of open spaces between the ribs that form the radial pattern;

wherein the scaffold is dimensioned and configured to repair or replace a damaged or missing tympanic membrane.

2. The device of claim 1, wherein the plurality of open spaces between the ribs of the scaffold forming the radial pattern are filled with the first material or combination of materials, or a second material or combination of materials.

3. The device of claim 1, wherein a plurality of the ribs of the scaffold are formed in a hub and spoke arrangement or in a group of concentric geometric shapes.

4. The device of claim 1, wherein the artificial tympanic membrane forms a circular 3-dimensional cone shape.

5. The device of claim 1, wherein the first material comprises one or more of polydimethylsiloxane (PDMS), hyaluronic acid (HA), poly(glycolic acid) (PGA), poly (lactic-co-glycolic acid) (PLGA), polylactic acid (PLA), polyester carbonate urethane urea (PECUU), poly octamethylene maleate anhydride citrate (POMaC), poly(glycerol sebacate) (PGS), poly(octanediol-co-citrate)(POC), polyurethane, collagen, fibrin, extracellular matrix, nylon, silk, poliglecaprone, and elastin.

6. The device of claim 1, wherein the second material comprises one or more of collagen, extracellular matrix, hydrogels, titanium dioxide, cellulose, gelatin, agarose, alginate, poly(N-isopropylacrylamide), hyaluronic acid, poly (vinyl alcohol)(PVA), poly (acrylic acid)(PAA), polycaprolactone, poly(3-hydroxybuterate-co-3-hydroxyvalerate, pluronic PLA, PGA, transglutaminase, PLGA, PDMS, poliglecaprone, polyester carbonate urethane urea (PECUU), poly octamethylene maleate anhydride citrate (POMaC), poly(glycerol sebacate)(PGS), poly(octanediol-co-citrate)(POC), polyurethane, and a mixture of collagen and fibrin.

7. The device of claim 1, further comprising a cellular adhesion-inducing material, a cellular invasion-inducing material, a growth factor, small molecules, biologics, a drug or drug-eluting material, or any combination thereof.

8. The device of claim 7, further comprising one or more types of cells selected from the group of types of cells consisting of fibroblasts, chondrocytes, keratinocytes, stem cells, progenitor cells, and epithelial cells.

9. The device of claim 1, wherein the device has a diameter based on a diameter of a natural tympanic membrane, or a perforation or defect in a natural tympanic membrane of a specific patient.

10. The device of claim 1, wherein the device has a thickness of 10 to 800 microns, and wherein the cone shape, if present, has a central height of up to about 3 mm.

11. The device of claim 1, wherein the device is impermeable to air or liquids.

12. The device of claim 1, wherein the device is permeable to any one or more of small molecules, biologics, steroids, and antibiotics.

13. The device of claim 1, further comprising an ossicular connector on one surface of the tympanic membrane graft, wherein the ossicular connector is formed as an artificial umbo and takes the shape of one of an umbo, a ring, a loop, a hinge, and a ball and socket.

14. A method of implanting the artificial tympanic membrane device of claim 1 into a patient to heal or augment a damaged tympanic membrane or to replace a missing tympanic membrane or missing portion thereof, the method comprising accessing the damaged or missing tympanic membrane;

obtaining an appropriately sized and configured artificial tympanic membrane device; and securing the artificial tympanic membrane device to seal the damaged portion of the tympanic membrane or replacing the missing tympanic membrane or missing portion thereof.

15. A bilayer tympanic membrane device comprising a pair of artificial tympanic membrane devices of claim 1, wherein a first of the pair of artificial tympanic membrane devices further comprises a projection, and wherein a second of the pair of artificial tympanic membrane devices further comprises an opening configured to enable insertion of the projection, wherein the first and the second tympanic membrane devices can be secured to each other to form the bilayer tympanic membrane device, wherein the projection and opening are dimensioned and configured to permit a tympanic membrane to be sandwiched between the two artificial tympanic membrane devices.

16. The bilayer tympanic membrane device of claim 15, wherein the opening and the projection comprise a lock and key configuration, a socket and ball configuration, or an opening and hinge configuration.

17. A method of fabricating an artificial tympanic membrane device, the method comprising:

forming a scaffold comprising a plurality of ribs using a first material, wherein the scaffold is approximately flat or has a shallow cone shape and a diameter of about 0.5 to about 19 millimeters, wherein at least one rib of the scaffold forms a circular shape and at least two ribs of the scaffold form a radial pattern, and wherein the ribs have a diameter of about 5 to about 800 microns; and wherein one or more open spaces are formed between the ribs that form the radial pattern, wherein the scaffold is dimensioned and configured to repair or replace a damaged or missing tympanic membrane.

18. The method of claim 17, wherein forming the scaffold comprises printing the scaffold with a three-dimensional (3D) printer onto a substrate.

19. The method of claim 17, further comprising forming a thin membrane in the open spaces between the ribs using the first material, a second material, or a combination of the first material and the second material.

20. The method of claim 19, wherein forming the thin membrane in the open spaces between the ribs comprises filling the open spaces with the first or the second material.

21. A method to repair a tympanic membrane perforation, the method comprising (a) obtaining first and second artificial tympanic membrane devices, wherein the first artificial tympanic membrane device comprises a projection, and wherein the second artificial tympanic membrane device comprises an opening configured to enable insertion of the projection;

(b) inserting the first artificial tympanic membrane device as an underlay device through the perforation in the tympanic membrane and securing a surface of the underlay device to the tympanic membrane such that the projection protrudes through the perforation;

(c) applying the second artificial tympanic membrane device as an overlay device over the perforation such that the projection protrudes through the perforation and through the opening of the overlay device and extends beyond a surface of the overlay device; and (d) moving one or both of the overlay device and the underlay device with respect to each other such that a portion of the projection is securely fit onto the surface of the overlay device to lock the underlay and overlay devices together, sandwiching the tympanic membrane between the underlay device and the overlay device.

22. The method of claim 21, wherein the top surface of the underlay device is adhered to the inner surface of the tympanic membrane by capillary action or adhesion, or a tissue adhesive, such as a fibrin glue.

23. The method of claim 21, wherein each of the artificial tympanic membrane devices comprises a scaffold comprising a plurality of ribs comprising a first material or combination of materials, wherein the scaffold is approximately flat or has a shallow cone shape and a diameter of about 0.5 to about 19 millimeters, wherein at least one of the ribs of the scaffold forms a circular shape and two or more ribs of the scaffold form a radial pattern, and wherein the ribs have a diameter of about 5 to about 800 microns; and a plurality of open spaces between the ribs that form the radial pattern.

* * * * *

UNITED STATES PATENT AND TRADEMARK OFFICE
CERTIFICATE OF CORRECTION

PATENT NO. : 10,786,349 B2  
APPLICATION NO. : 15/559582  
DATED : September 29, 2020  
INVENTOR(S) : Aaron K. Remenschneider et al.

Page 1 of 1

It is certified that error appears in the above-identified patent and that said Letters Patent is hereby corrected as shown below:

In the Specification

In Column 1, Line 9, delete "2017," and insert -- 2016, --

In the Claims

In Column 29, Line 38, Claim 6, delete "-hydroxybuterate-" and insert -- -hydroxybutyrate- --

Signed and Sealed this  
First Day of December, 2020

Andrei Iancu  
*Director of the United States Patent and Trademark Office*